US007530948B2

(12) United States Patent
Seibel et al.

(10) Patent No.: US 7,530,948 B2
(45) Date of Patent: May 12, 2009

(54) TETHERED CAPSULE ENDOSCOPE FOR BARRETT'S ESOPHAGUS SCREENING

(75) Inventors: Eric J. Seibel, Seattle, WA (US); Michael Kimmey, Seattle, WA (US); Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 789 days.

(21) Appl. No.: 11/069,826

(22) Filed: Feb. 28, 2005

(65) Prior Publication Data

US 2006/0195014 A1 Aug. 31, 2006

(51) Int. Cl.
A61B 1/005 (2006.01)
A61B 1/07 (2006.01)

(52) U.S. Cl. ........................ 600/178; 600/129; 600/173; 600/476

(58) Field of Classification Search ................. 600/178, 600/173, 182, 176, 177, 129, 476–478
See application file for complete search history.

(56) References Cited

U.S. PATENT DOCUMENTS

| | | | | |
|---|---|---|---|---|
| 5,643,175 A * | 7/1997 | Adair | ................... | 600/133 |
| 6,035,229 A | 3/2000 | Silverstein et al. | ............ | 600/473 |
| 6,134,003 A * | 10/2000 | Tearney et al. | ............ | 356/479 |
| 6,185,443 B1 | 2/2001 | Crowley | ................... | 600/407 |
| 6,240,312 B1 * | 5/2001 | Alfano et al. | ................ | 600/476 |
| 6,485,413 B1 | 11/2002 | Boppart et al. | .............. | 600/160 |
| 2002/0091325 A1 * | 7/2002 | Ostrovsky | ................... | 600/478 |
| 2003/0060734 A1 * | 3/2003 | Yokoi et al. | .................. | 600/593 |
| 2003/0181788 A1 * | 9/2003 | Yokoi et al. | .................. | 600/160 |
| 2003/0208134 A1 | 11/2003 | Secrest et al. | ............... | 600/562 |
| 2004/0176683 A1 | 9/2004 | Whitin et al. | ............... | 600/424 |
| 2005/0183733 A1 * | 8/2005 | Kawano et al. | ............. | 128/899 |
| 2005/0215911 A1 * | 9/2005 | Alfano et al. | ................ | 600/476 |
| 2008/0161748 A1 * | 7/2008 | Tolkoff et al. | .................. | 604/21 |

OTHER PUBLICATIONS

Given Imaging Web page. Given® Diagnostic System, The Platform for PillCam™ Endoscopy. ©2001-2004. www.givenimaging.com. 4pp.

* cited by examiner

*Primary Examiner*—John P Leubecker
(74) *Attorney, Agent, or Firm*—Ronald M. Anderson

(57) ABSTRACT

A capsule is coupled to a tether that is manipulated to position the capsule and a scanner included within the capsule at a desired location within a lumen in a patient's body. Images produced by the scanner can be used to detect Barrett's Esophagus (BE) and early (asymptomatic) esophageal cancer after the capsule is swallowed and positioned with the tether to enable the scanner in the capsule to scan a region of the esophagus above the stomach to detect a characteristic dark pink color indicative of BE. The scanner moves in a desired pattern to illuminate a portion of the inner surface. Light from the inner surface is then received by detectors in the capsule, or conveyed externally through a waveguide to external detectors. Electrical signals are applied to energize an actuator that moves the scanner. The capsule can also be used for diagnostic and/or therapeutic purposes in other lumens.

67 Claims, 17 Drawing Sheets

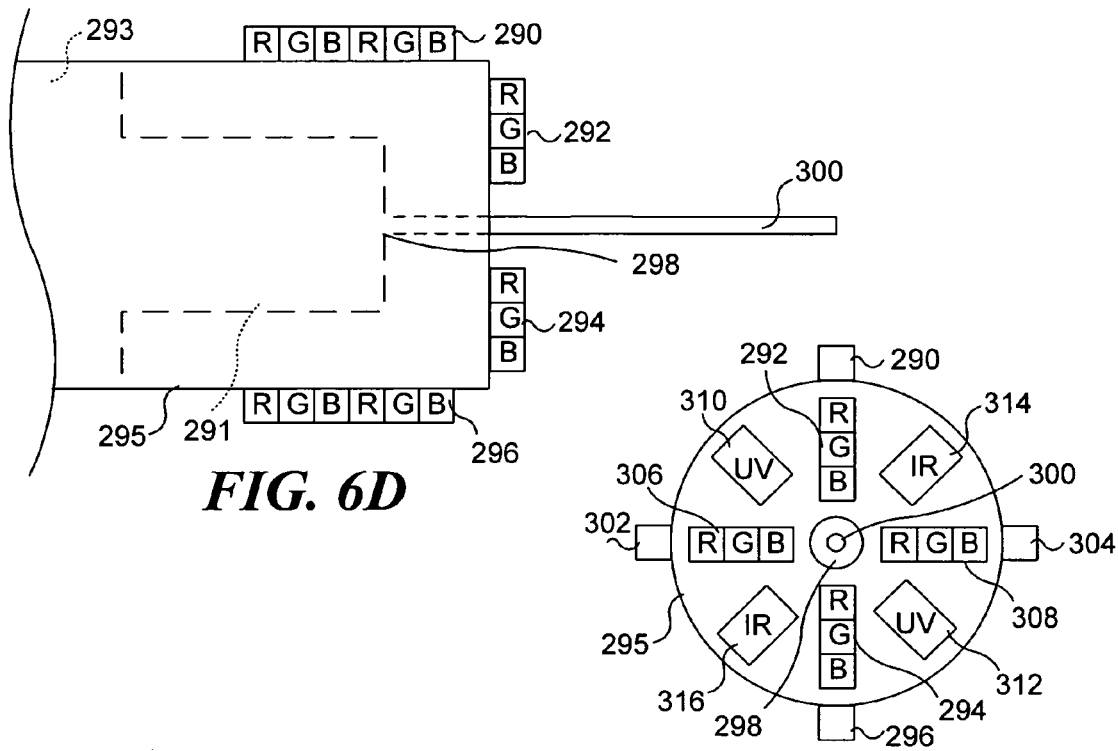
*FIG. 6D*
*FIG. 6E*
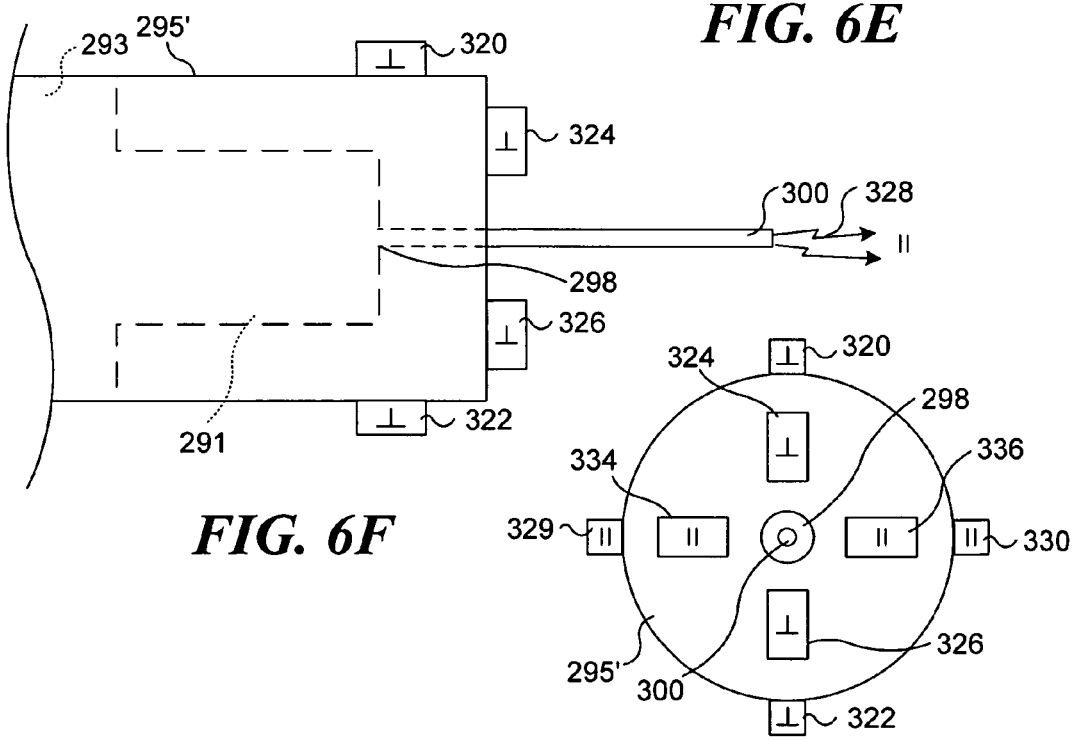
*FIG. 6F*
*FIG. 6G*

TETHERED CAPSULE ENDOSCOPE FOR BARRETT'S ESOPHAGUS SCREENING

FIELD OF THE INVENTION

The present invention generally pertains to apparatus and a method for diagnostic imaging within a body lumen using a scanning endoscope that is housed in a capsule, and more specifically, pertains to apparatus and a method for imaging an internal wall of the lumen with an imaging capsule to detect a medical condition, where the capsule is electronically coupled to an external data receiver through a tether lead that is also used to control the location of the capsule within the lumen.

BACKGROUND OF THE INVENTION

Barrett's Esophagus (BE) is a condition of the esophagus that is pre-cancerous, a precursor to cancer of the esophagus. The standard practice for diagnosing Barrett's Esophagus is using flexible endoscopy, often with the esophageal lumen insufflated with air. A normal esophagus is usually light pink in color, while the stomach appears slightly darker pink. Barrett's Esophagus usually manifests itself as regions of slightly darker pink color above the lower esophageal sphincter (LES) that separates the stomach from the esophagus. It is preferable to diagnose Barrett's Esophagus early, since this condition has often been found to be a precursor of esophageal adenocarcinoma. Accordingly, it would be desirable to screen for the condition, even though that would require evaluating the condition of the esophagus in millions of people with chronic heartburn and gastric reflux. However, Barrett's Esophagus and early stage cancers can occur without telltale symptoms, so mass screenings have been proposed as the only viable approach to identify the condition as early as possible to enable treatment and avoid the onset of or provide a curative therapy for the cancerous condition. However, the numbers of people that are likely candidates for esophageal screening and the current cost associated with the practice of flexible endoscopy performed by a physician compared to the reimbursement associated with such mass screenings make this solution currently impractical.

What is needed is a much more efficient and cost effective approach for identifying those people having Barrett's Esophagus. Only a doctor can perform an examination of the esophagus using a conventional flexible endoscope, and the procedure is thus relatively expensive. It would be preferable to develop a different scanning technique that need not be performed by a physician, but instead, can be performed by a trained medical technician or nurse. Indeed, it would also be desirable to automate the evaluation of images produced by imaging the internal surface of the esophagus just proximal of the LES so that the existence of Barrett's Esophagus can be automatically detected either in real time during the scanning operation or immediately thereafter.

To facilitate mass screenings of individuals who may be afflicted with Barrett's Esophagus, it would be desirable to employ a screening device that can readily be introduced into the esophagus, without invoking any gag reflex. Ideally, the scanning device should be embodied in a capsule-shaped housing so that it can simply be swallowed with a glass of water. Accordingly, the device must be sufficiently small in size to enable it to be swallowed by most patients. Further, although such a device might be reusable if properly sterilized, it will likely be preferable to employ a screening device that is sufficiently low in cost as to be disposable after a single use.

An Israeli company, Given Imaging Ltd., has developed a swallowable camera battery-powered capsule that is used in connection with a harness that receives imaging signals transmitted from the capsule. Batteries in the harness are used to provide power for image storage and for a receiver included in the harness that receives a radio signal from a transmitter in the camera capsule. The harness of the camera capsule is worn like a belt while the patient goes about their normal activity during about an eight hour period. The capsule and camera passes through the entire gastrointestinal tract and is expelled with other wastes in a normal fashion. Images taken by the camera and wirelessly transmitted to a receiver on the harness can then be viewed in an attempt to identify various medical conditions in the patient's gastrointestinal tract. The camera-capsule thus provides images of portions of the small intestine that are beyond the reach of a conventional endoscopy using an endoscope, or colonoscope. However, there is no control on the rate at which the camera-capsule moves through the gastrointestinal tract. Also, its position within the gastrointestinal tract is not readily determined. An earlier version of this capsule system has been modified to include a lens on each end of the capsule and to acquire images at a greater frame rate, specifically for imaging the esophagus. This system is still quite expensive and does not enable control of the capsule location by the operator.

Therefore, in addition to providing a scanning device that is useful in scanning the general population for Barrett's Esophagus, it would be desirable to use such a scanning device in many other procedures that require imaging of an interior surface within a body lumen. It would be desirable to control the disposition of the scanning device within the lumen and to enable it to advance based upon muscle tissue action in the wall of the lumen, but to be controlled or even withdrawn back along the path of its travel. Currently, there are scanners that are sufficiently small, but none have yet been provided in a capsule that meets the other desired criteria for imaging internal surfaces within a lumen.

SUMMARY OF THE INVENTION

Accordingly, a first aspect of the present invention is directed to apparatus for imaging an inner surface of a lumen in a patient's body. The apparatus includes a capsule housing that is sized to readily pass through the lumen. An imaging portion of the capsule housing is optically transparent to enable scanning through that portion to image the inner surface of the lumen. A light source is included and can be either disposed externally of the lumen or internally within the capsule housing. Disposed within the capsule housing is a scanner having an actuator. The actuator drives the scanner to scan the inner surface of the lumen in a desired scanning pattern with a beam of light from the scanner. At least one light sensor is included and responds to light that has been reflected from the inner surface of the lumen. Each such light sensor produces an electrical signal that is indicative of an intensity of the light. An optical system included on the apparatus focuses the light emitted from the scanner onto a portion of an inner surface of a lumen in a patient's body. Connected to the capsule housing is a tether that extends proximally through the lumen. The tether enables a force to be applied to the capsule housing to control its movement within the lumen.

In one embodiment, the at least one light sensor is disposed external to the capsule housing. In another embodiment, light reflected from the inner surface of the lumen is conveyed through an optically transmissive channel included within the tether to the at least one light sensor, which is disposed proximal of the capsule housing, e.g., outside the patient's body. The optically transmissive channel can be a core of an optical fiber that comprises the tether, or a core of an optical fiber that also conveys light from the light source through the tether and into the capsule housing, or a cladding of an optical fiber that comprises the tether.

In the embodiment in which the at least one light sensor is disposed within the capsule housing, the light reflected from an inner surface of a lumen is received by the at least one light sensor, which produces a corresponding electrical signal. In one embodiment, the tether includes at least one electrical lead that is coupled to the light sensor and conveys the electrical signal that it produces to a location that is outside of the lumen.

In one embodiment, the scanner can include a scanning mirror that is driven by the actuator to reflect the light produced by the light source, in the desired scanning pattern. In another embodiment, the scanner comprises a waveguide that is driven to move by the actuator, so that the waveguide emits light from a distal end of the waveguide, to scan in the desired pattern.

Various other functional aspects can be provided on the capsule housing. For example, a pressure sensor can be disposed on the capsule housing for monitoring a pressure applied to the capsule, producing a pressure signal indicative of the pressure. Also, a location sensor can be included for monitoring a location of the capsule housing within a lumen, relative to a reference point. As another option, a chemical sensor can be included for monitoring at least one chemical parameter from within a lumen of a patient's body, such as pH. As a still further function, means can be included on the capsule housing for performing a biopsy, i.e., to take a tissue sample at a desired site within the lumen.

The capsule housing is normally advanced through the lumen by the natural action of the lumen walls. However, it is also noted that the apparatus can include at least one electrical contact disposed on an exterior of the capsule housing, to stimulate muscle tissue in a wall of the lumen, to promote peristalsis for more efficiently moving the capsule housing through the lumen.

To enable a user to measure a distance traveled by the capsule housing into the lumen, the tether can be provided with a plurality of scale markings. Or, the apparatus may include a rotary component engaged by the tether that is rotated as the capsule housing moves through the lumen. The rotary component is thus used to provide an indication of the distance traveled by the capsule housing into a lumen. In one embodiment wherein the lumen is the esophagus, the apparatus includes a bite bar that is adapted to be disposed in a mouth of a patient to support the rotary component, so as to ensure a reproducible tracking of the distance through which the capsule housing moves within the esophagus. It may be desirable to include a joint for selectively releasably connecting to the tether and disposed either adjacent to the capsule housing, or adjacent to the bite bar.

In one embodiment, the optics system includes at least one reflective surface for directing the light emitted from the scanner laterally to a side of the capsule housing. The optical system can include at least one lens disposed between the scanner and the imaging portion of the capsule. In addition, in one embodiment, the optical system includes at least one filter that is disposed so as to filter light that is either produced by the scanner and directed to an internal surface of the lumen, or reflected from an internal surface of the lumen before the light is sensed by the at least one light sensor.

Preferably, the imaging portion of the capsule is disposed at a distal end of the capsule housing; and the tether is connected to a proximal end of the capsule housing.

The scanner can include either a single mode optical fiber, a dual cladding optical fiber, a single mode optical fiber used for conveying light from the light source, and at least one multimode collection optical fiber for conveying light reflected from an inner surface of a lumen to the at least one light sensor, or a waveguide comprising a microelectromechanical system (MEMS) device. In one preferred embodiment, the scanner comprises either a waveguide or an optical fiber that is driven by the actuator to move at about a resonant frequency when scanning in the desired pattern. Optionally, a feedback sensor is included for controlling a movement of the waveguide or the optical fiber, so as to substantially reduce any distortion in an image produced by scanning with the light beam produced thereby. The actuator preferably comprises an electromechanical actuator that produces a driving force in a plurality of orthogonal directions, to achieve the desired pattern for scanning the internal surface of the lumen.

Optionally, the at least one light sensor actually comprises a plurality of light sensors, including light sensors that are responsive to light of different spectral wavebands, and/or to polarized light.

To ensure good imaging coverage, the optical system can be configured to direct the light emitted by the scanner through the imaging portion of the capsule housing, so that the desired scanning pattern illuminates the interior surface of the lumen over substantially an entire 360 degree arc, distally of the capsule housing. For example, a plurality of scanners can be disposed within the capsule housing, each scanner including a separate actuator and being configured to scan a different part of the inner surface of the lumen. Indeed, the plurality of scanners can be configured to increase a field of view compared to a field of view provided by a single scanner, or scan an inner surface of a lumen from opposite ends of the capsule housing, or provide a stereo scan image of an inner surface of a lumen, or perform a diagnostic scan an inner surface of a lumen using light of a predefined waveband, or provide a therapeutic scan of an inner surface of a lumen using light from at least one of the plurality of scanners, or monitor a state of a therapy being applied within a lumen, or provide illumination used to measure distance between one scanner and an inner surface of a lumen. In one embodiment, the plurality of scanners are spaced apart in an array within the capsule housing, and the optical system directs the light emitted from each scanner to the different part of the inner surface of the lumen.

Preferably, the capsule housing is sized and configured to be swallowed by a patient with the tether connected thereto. The apparatus can include a data recording medium that receives an electrical signal from the at least one light sensor and stores data corresponding to the electrical signal produced by the at least one light sensor. The data can represent a plurality of image frames that are readily combined to produce at least one continuous two-dimensional image of the inner surface of the lumen.

Another option is a spectral analyzer that analyzes an electrical signal produced by the at least one light sensor. The waveband of the spectral analyzer is in a desired range that is selected from a waveband range extending from the ultraviolet to the infrared wavebands.

An inflatable balloon is coupled to the capsule in one embodiment. The balloon, when inflated, can be used for several different functions. For example, the inflated balloon can be used to enable peristaltic advancement of the balloon and capsule through the lumen, in response to forces applied by the lumen on the balloon. The balloon can also convey a fluid pressure from a wall of a lumen in which the balloon is disposed, to a pressure sensor that enables a pressure exerted thereby on the balloon to be monitored. Alternatively, the balloon can be inflated to enlarge a cross-sectional size of the balloon and the capsule housing in combination, thereby preventing further movement of the capsule housing through the lumen, because the cross-sectional size of the lumen is smaller than that of the balloon. As a further function, the inflated balloon can be employed to generally center the capsule housing within the lumen.

At some point, it may be desirable to enable the capsule housing to continue through the lumen. Accordingly, a disconnect can be provided that is selectively actuatable to release the capsule housing from the tether.

Another aspect of the present invention is directed to a capsular system for scanning an inner surface of a lumen in a patient's body, while yet another aspect is directed to a method for scanning an inner surface of a lumen in a patient's body. The capsular system includes components that are generally consistent with the apparatus discussed above, and the method carries out steps that make use of such a system.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 7A:
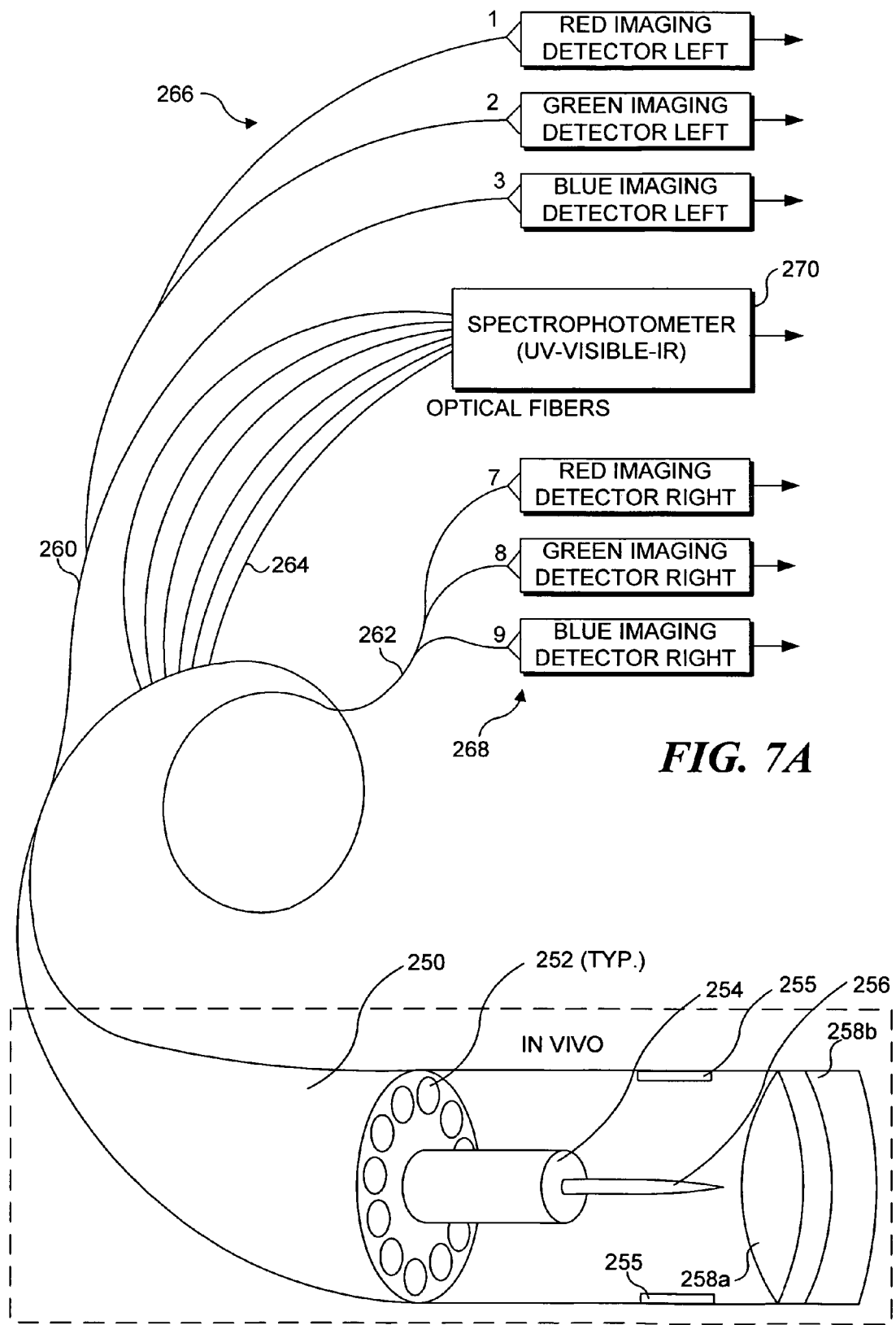
Figure 7B:
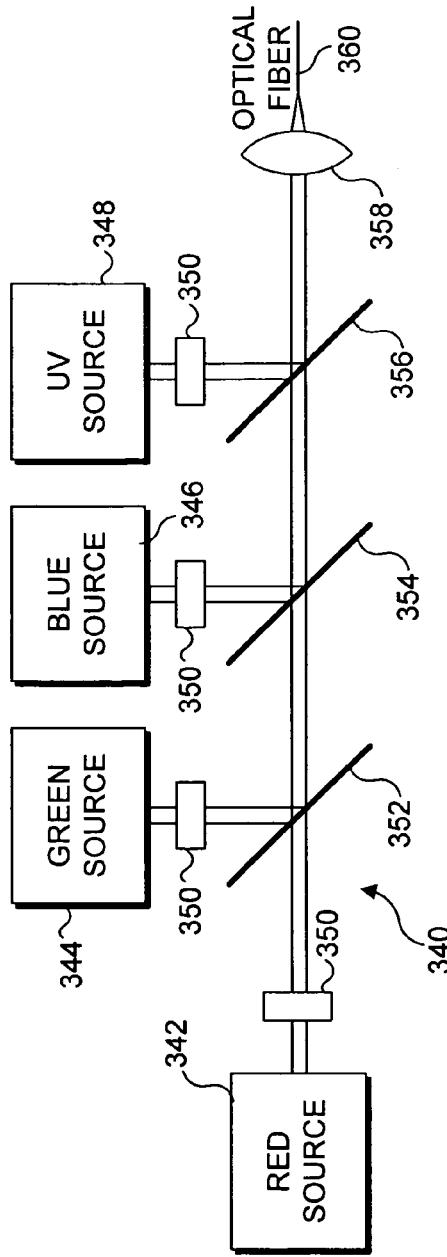
Figure 7C:
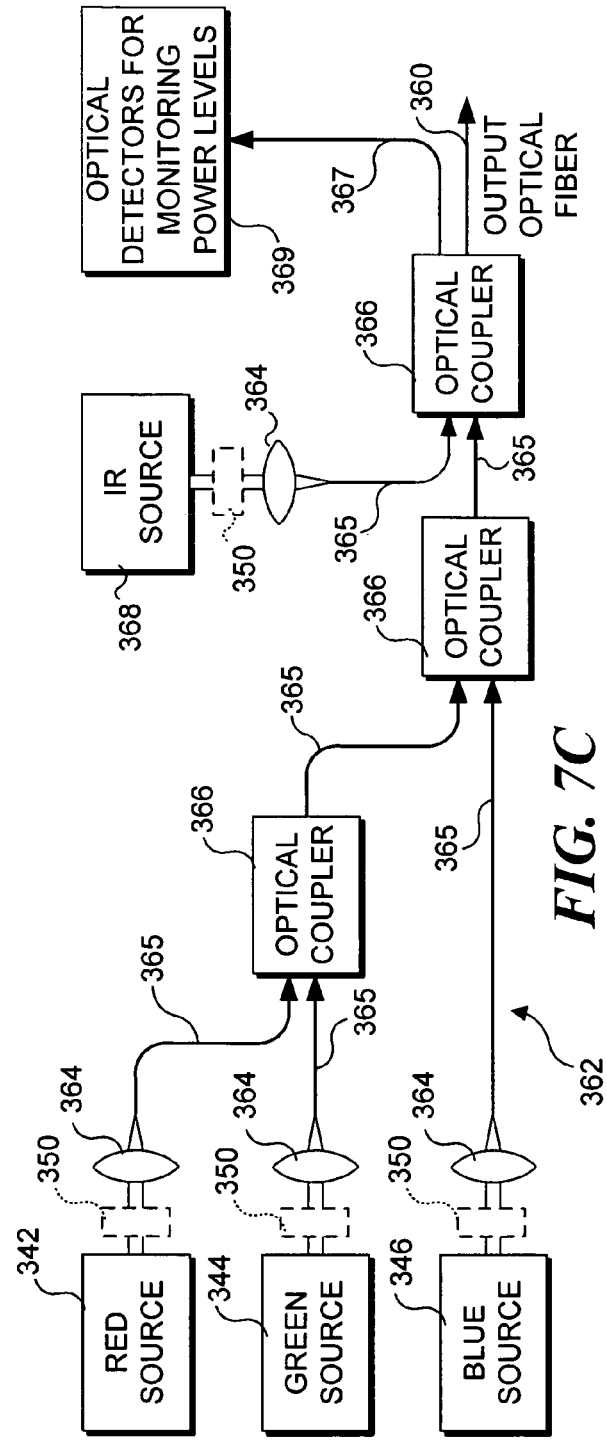
Figure 8A:
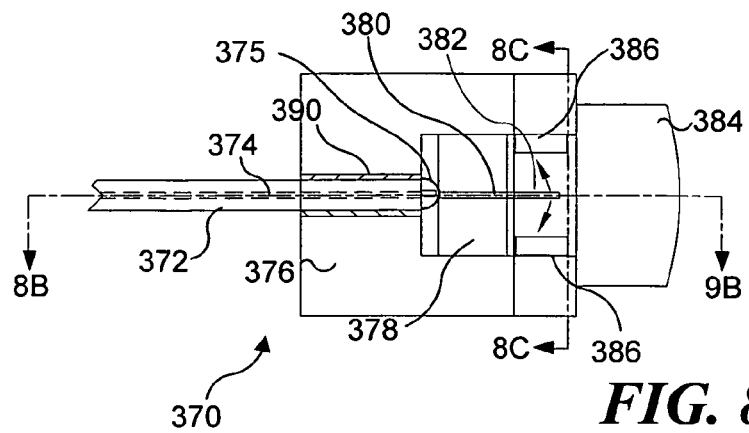
Figure 8B:
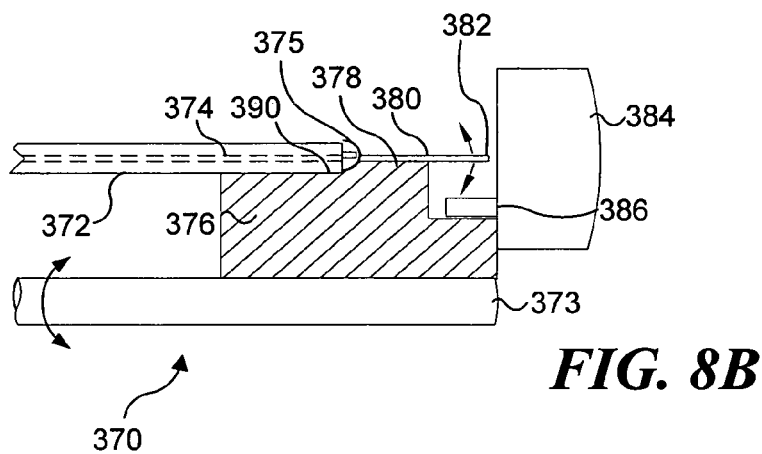
Figure 8C:
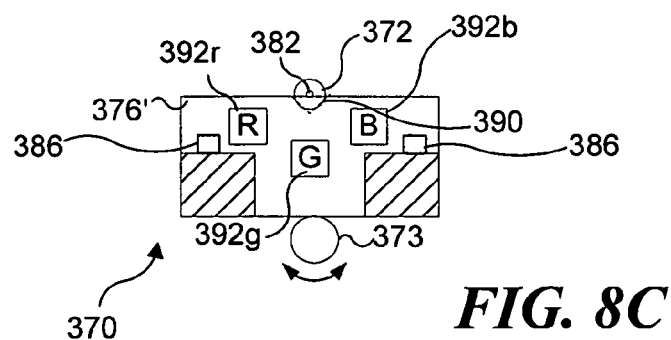
Figure 8D:
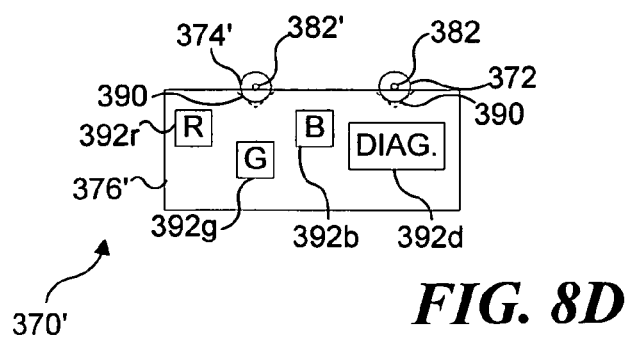
Figure 9:
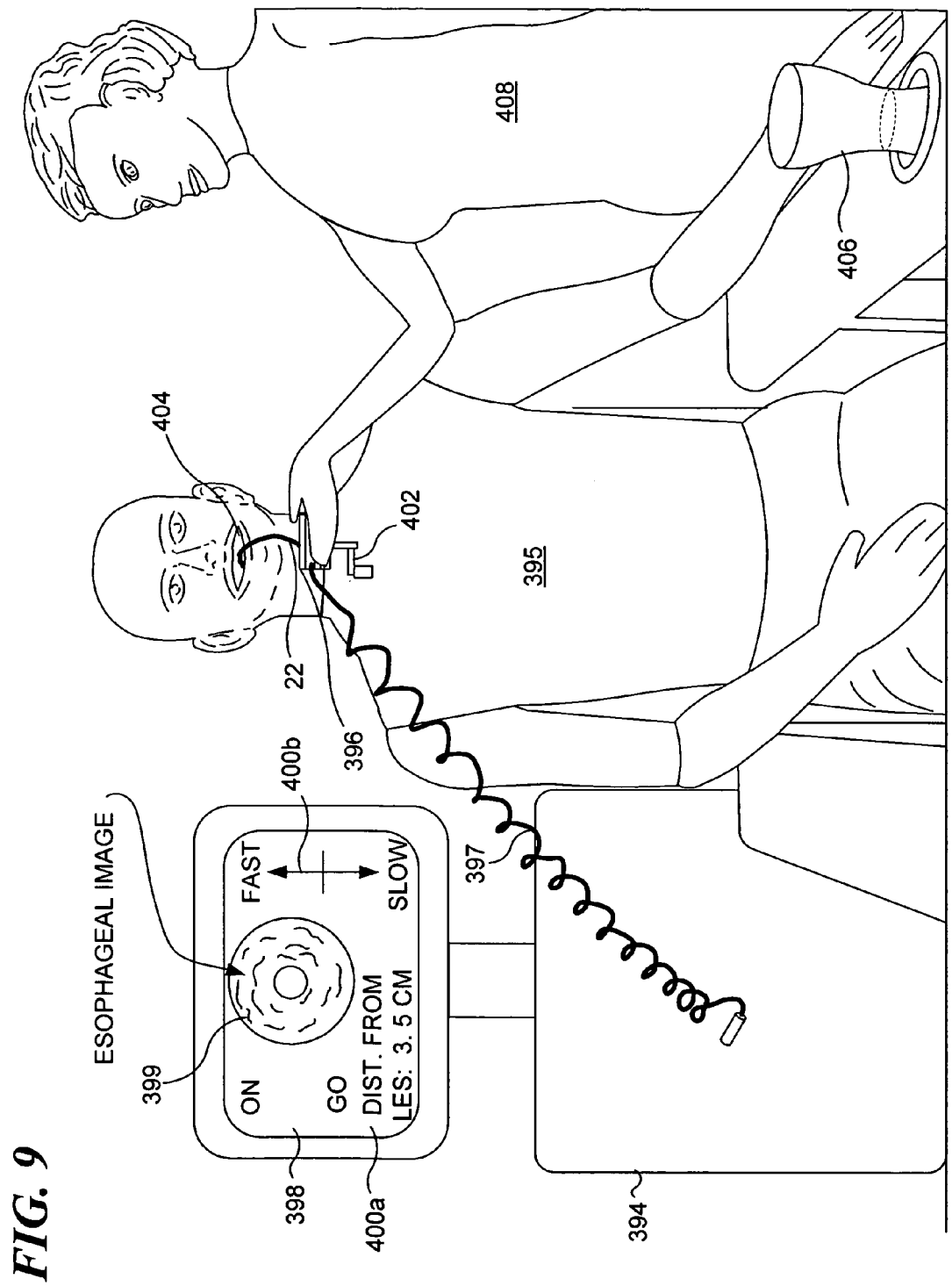
Figure 10:
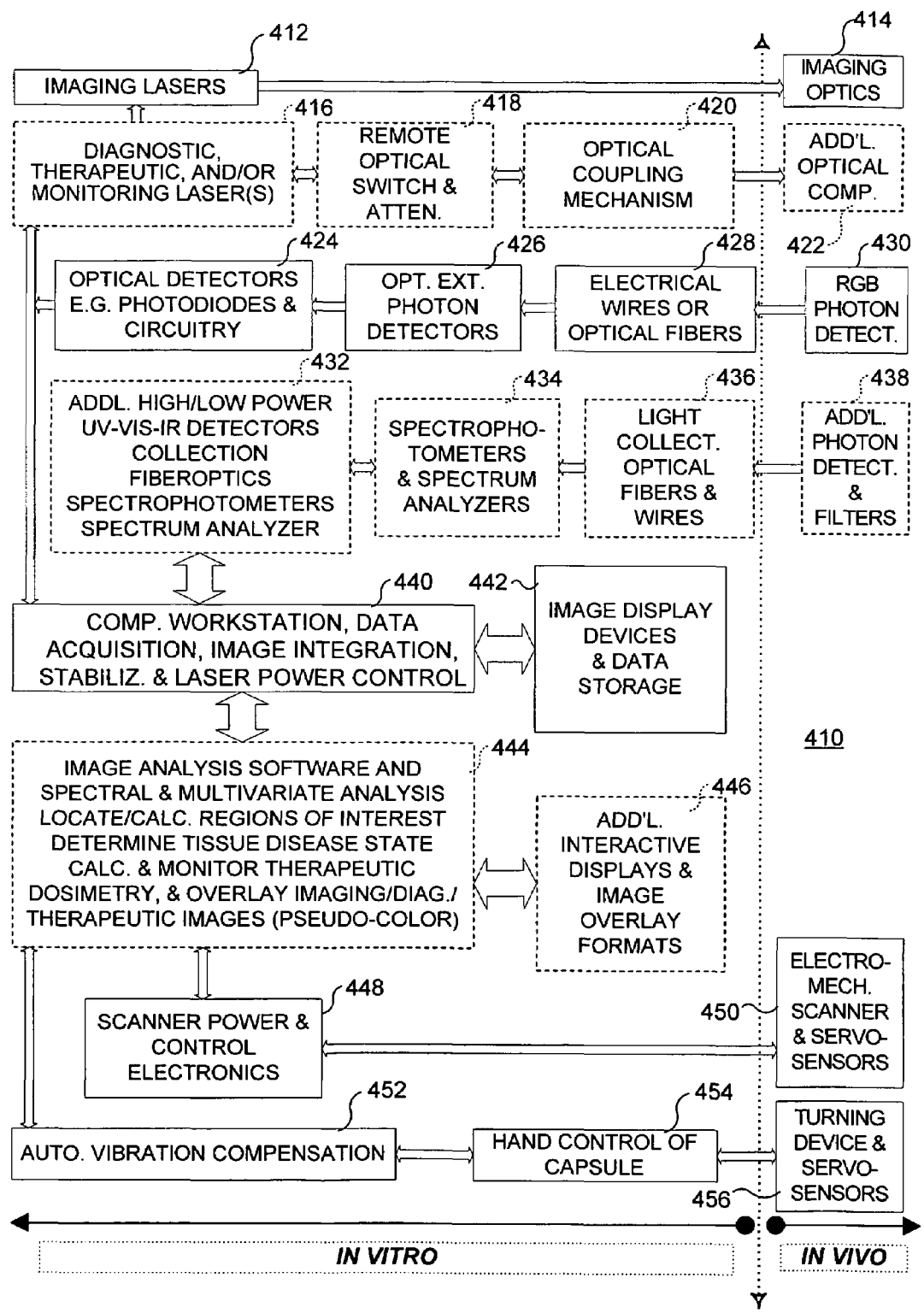
Figure 11A:
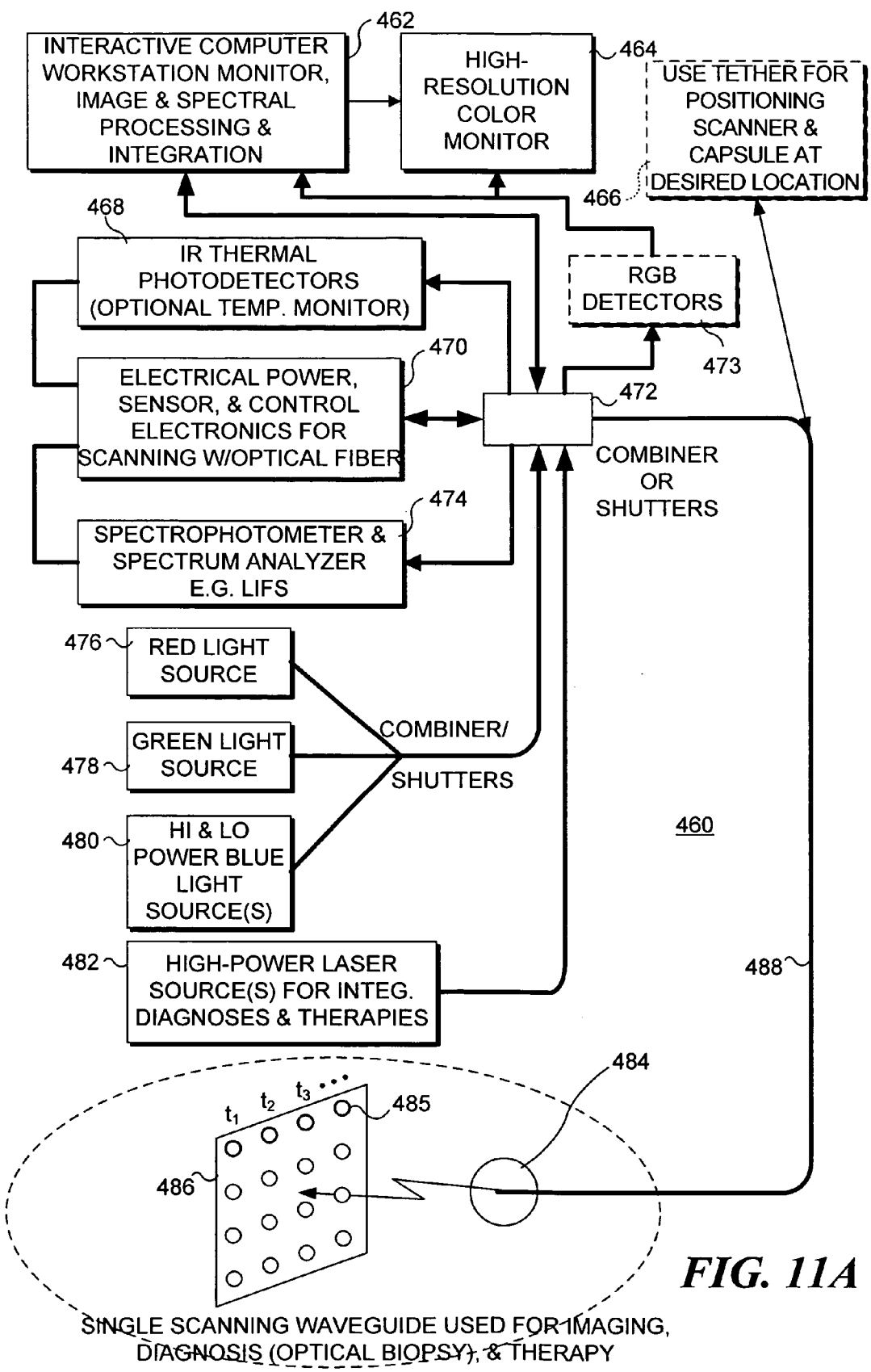
Figure 11B:
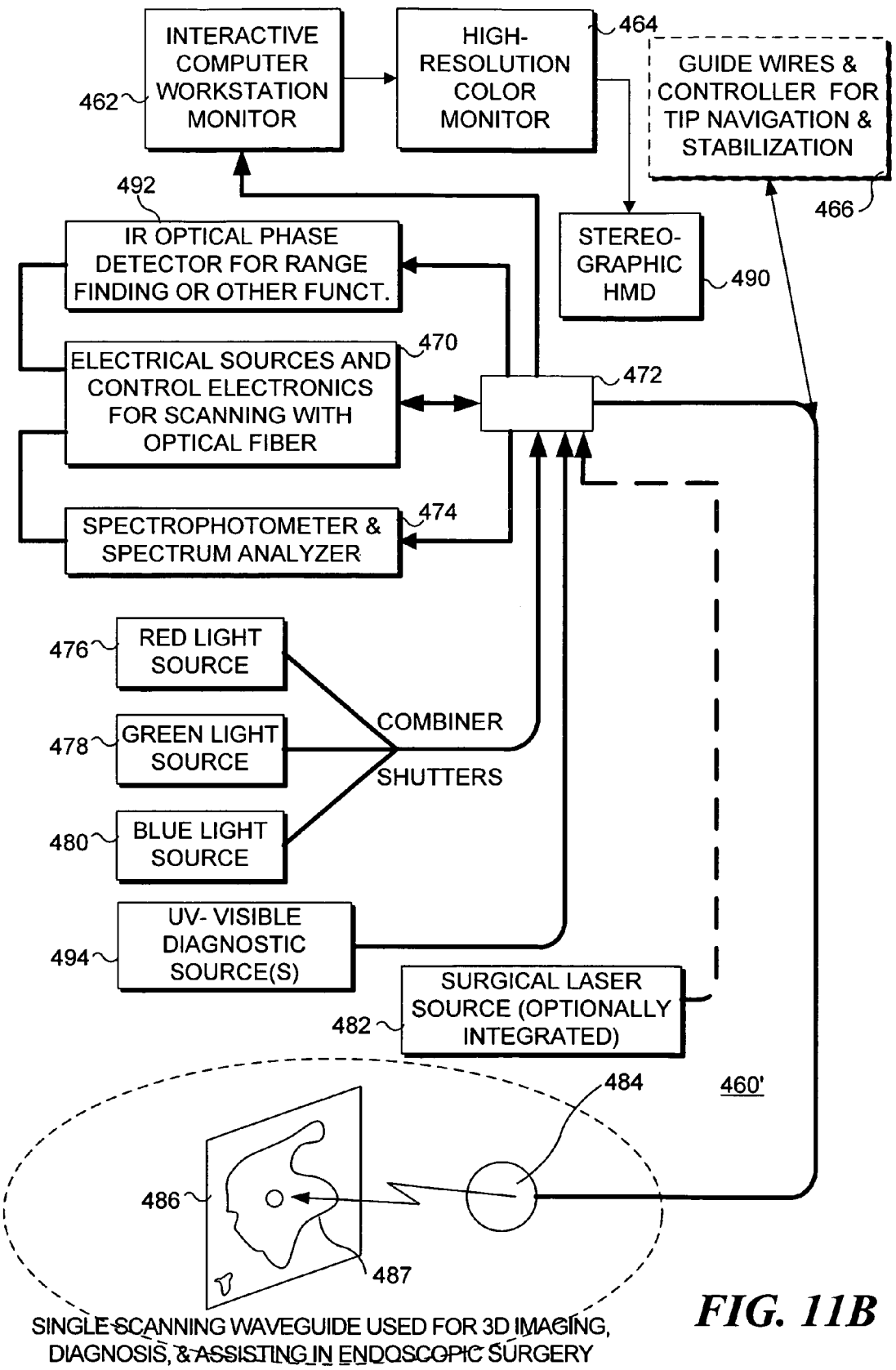
Figure 12A:
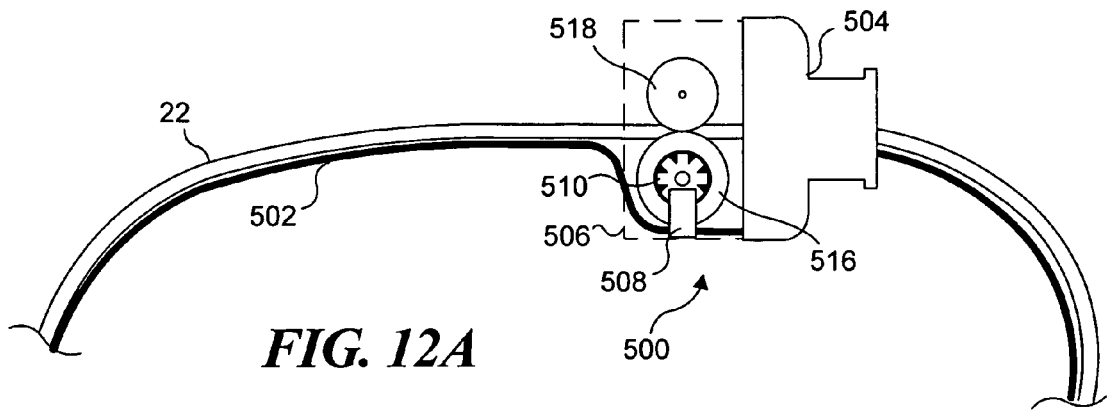
Figure 14:
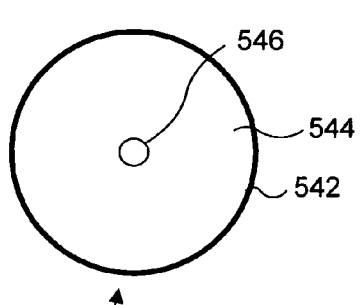
Figure 12B:
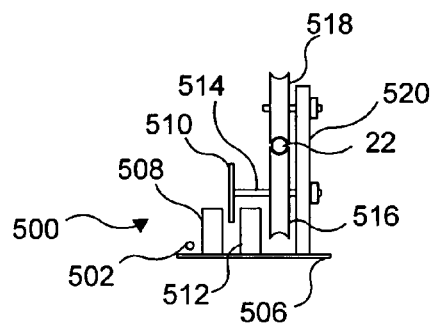
Figure 13:
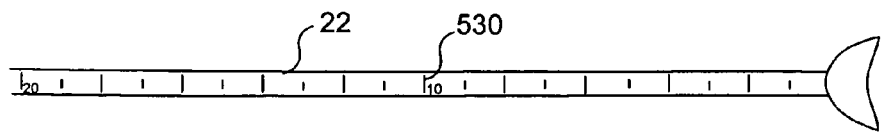
Figure 15:
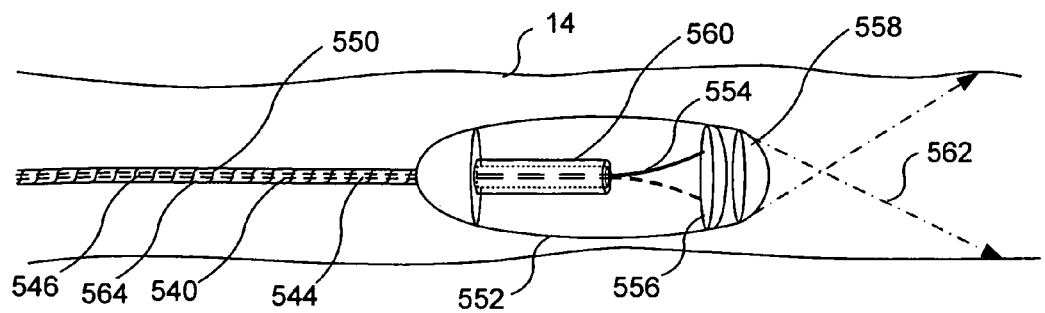
Figure 16:
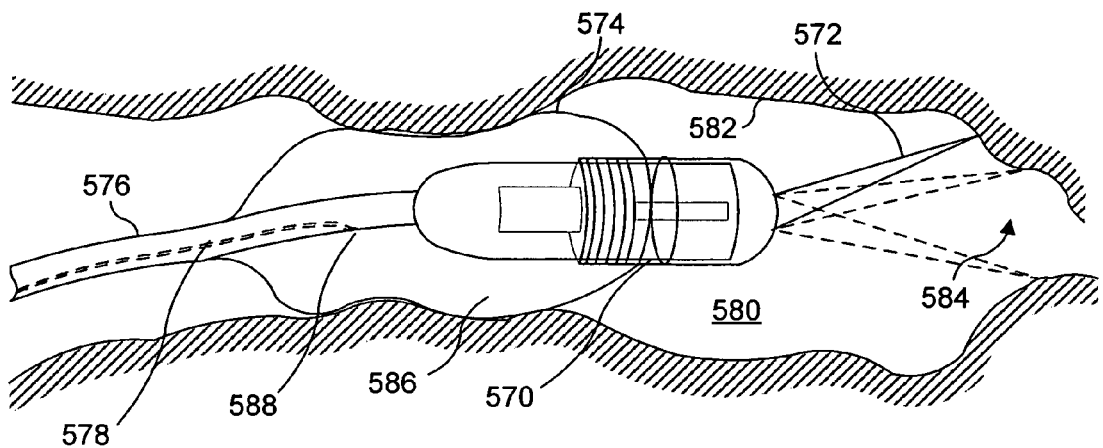
Figure 17:
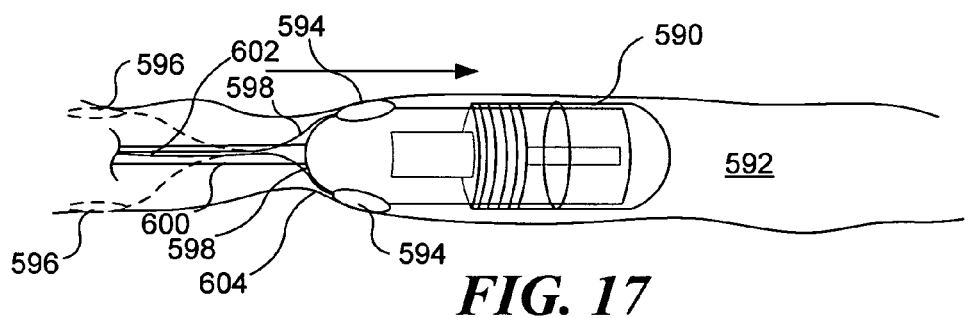
Figure 18:
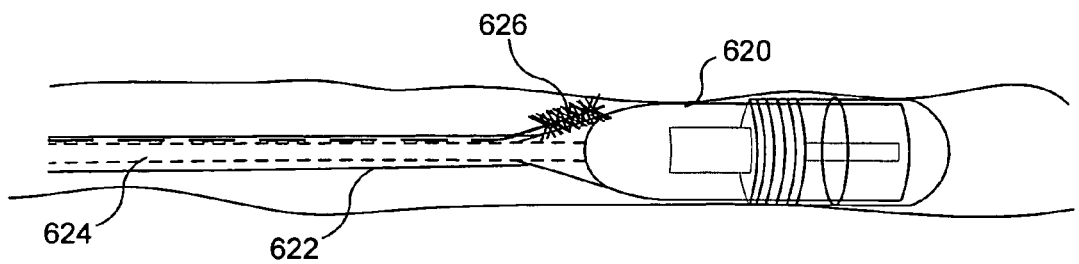
Figure 19:
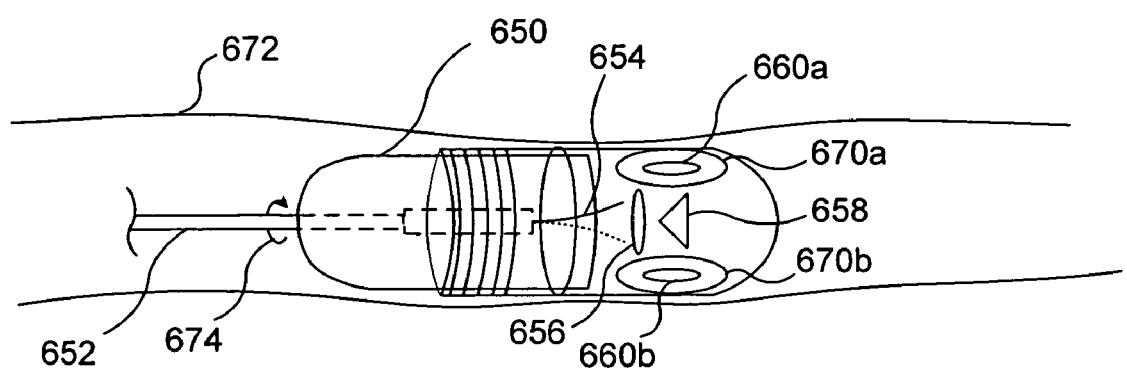

FIGS. 6D and 6E schematically illustrate a scanner having distal photon red, green, blue (RGB) filtration and detection using stereo-paired geometry and the ability to subtract background scatter using forward and side-facing spatial arrangements of detectors, respectively shown in a side elevational view and in an end view;

FIGS. 6F and 6G schematically illustrate a scanner having distal photon polarized filtration and detection using stereo-paired geometry and the ability to enhance signals from superficial tissue on the inner surface of a lumen, using forward and side-facing spatial arrangements of detectors, respectively shown in a side elevational view and in an end view;

FIG. 7A is a schematic diagram showing the configuration of a scanner with distal optical fiber position sensors and proximally disposed photon detectors with proximal optical fiber light collectors that are capable of pseudo-stereo image acquisition;

FIG. 7B is a schematic diagram of an optical fiber scanning system for use with the present invention, which employs radiation from visible and UV laser sources combined with dichroic filters;

FIG. 7C is a schematic diagram of an optical fiber system for use with the present invention, which employs radiation from visible and IR laser sources combined with fiber optic combiners connected in series;

FIGS. 8A, 8B, and 8C respectively illustrate a top plan view, a side elevational cross-sectional view taken along section line 8B-8B in FIG. 8A, and an end view taken along section line 8C-8C in FIG. 8A, of an embodiment of a thin film, microelectromechanical (MEMS) system scanner that is usable in the present invention;

FIG. 8D illustrates an end elevational view of another embodiment that includes a pair of thin film parallel cantilevers for illumination of an interior surface of a lumen;

FIG. 9 illustrates a medical practitioner using the present invention to carry out automated scanning and diagnostic evaluation of a patient's esophagus, such as might occur during mass screenings of the general population for BE;

FIG. 10 is a block diagram illustrating the functional input and output components of an optical fiber scanner system for use with the present invention;

FIG. 11A is a functional block diagram of an integrated cancer imaging, screening, and biopsy system, with optical therapy delivery and monitoring capabilities using a capsule and scanner in accord with the present invention;

FIG. 11B is a functional block diagram of an integrated cancer imaging and diagnostic system, with stereograph surgical support and display capabilities using a capsule and scanner in accord with the present invention;

FIGS. 12A and 12B respectively are schematic side and cross-sectional elevational views of a bite piece and measuring device for detecting the extent movement of the capsule into an esophagus of a patient;

FIG. 13 is a portion of a tether that includes markings for determining an extent of movement into a lumen by the capsule;

FIG. 14 is a cross-sectional view of a dual cladding optical fiber that is able to convey light to the scanner at a distal end of the optical fiber and also convey reflections proximally back from an inner surface of a lumen;

FIG. 15 is a schematic view of a capsule and scanner that employs the dual cladding optical fiber of FIG. 14;

FIG. 16 is a schematic view of a capsule having a balloon attached, wherein the balloon is shown inflated in a lumen;

FIG. 17 is a schematic view of a capsule having electrodes to cause muscle tissue peristalsis that advances the capsule through a lumen;

FIG. 18 is a schematic view of a capsule having a tether that includes an annular channel through which a biopsy instrument, such as a cytological brush is advanced to take a biopsy of tissue from an inner surface of a lumen; and FIG. 19 is a schematic view of a capsule having a pyramidal-shaped mirror for simultaneously laterally imaging opposite inner surfaces of a lumen, showing how the tether can be used to rotate the capsule as needed to encompass a full view of the inner surface of a lumen.

DESCRIPTION OF THE PREFERRED EMBODIMENT

Exemplary Application of Present Invention

Although the present invention was initially conceived as a solution for providing relatively low cost mass screening of the general population to detect Barrett's Esophagus without requiring interaction by a physician, it will be apparent that this invention is also generally applicable for use in scanning, diagnoses, rendering therapy, and monitoring the status of therapy thus delivered to an inner surface of almost any lumen in a patient's body. Accordingly, although the following discussion often emphasizes the application of the present invention in the detection of Barrett's Esophagus, it is intended that the scope of the invention not in any way be limited by this exemplary application of the invention.

Figure 1A:
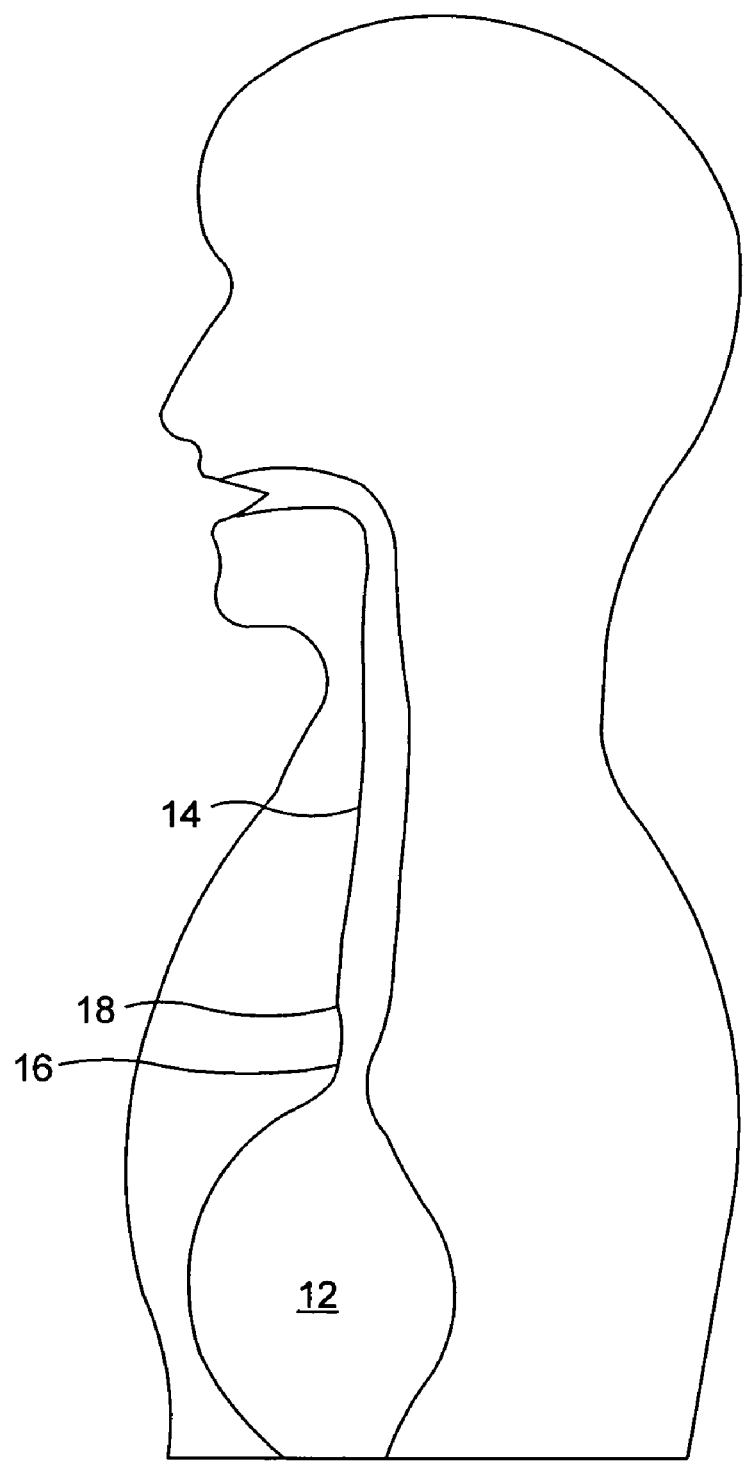
FIG. 1A is a schematic view showing an esophagus and stomach, to illustrate how one body lumen that can be readily scanned using the present invention.

FIG. 1A includes a schematic illustration 10 showing a stomach 12, an esophagus 14, and a lower esophageal sphincter (LES) 16. LES 16 normally acts as a one-way valve, opening to enable food swallowed down the esophagus 14 to pass freely into stomach 12, but normally preventing acid and food from moving back up into the esophagus 14 from inside stomach 12. However, as noted above in the Background of the Invention, people suffering from chronic heartburn and gastroesophageal reflux often experience Barrett's Esophagus as a result of stomach acid passing through LES 16 and into the lower part of esophagus 14. Patients who are suffering from Barrett's Esophagus can be detected by determining whether the inner surface of the lumen comprising esophagus 14 has changed from its normal light pink color to a dark pink color in a region 18 that is just above LES 16. The present invention enables region 18 within esophagus 14 to be readily scanned, producing images in which the presence of the darker pink color of the inner surface that is indicative of Barrett's Esophagus is clearly apparent. More importantly, as discussed in further detail below, the present invention is ultimately expected to enable the scanning process to be carried out in an automated fashion, so that the detection of Barrett's Esophagus can be accomplished by a medical practitioner, and normally without any direct interaction by a medical doctor.

Figure 1B:
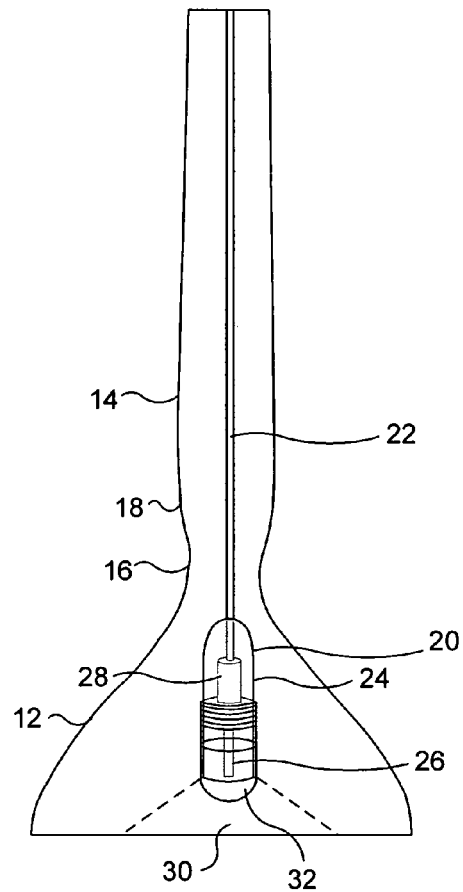
FIG. 1B is a schematic view of a portion of the esophagus and stomach of FIG. 1A, showing how the present invention is controllably disposed to scan a desired portion of the esophagus to detect a BE condition.

The manner in which the present invention is used in this exemplary application is illustrated in FIG. 1B. As shown therein, a capsule 20 that is sized and configured in accord with the present invention has been advanced through the interior of esophagus 14 and has just passed into stomach 12. Capsule 20 is coupled to a tether 22 that extends up through esophagus 14 and out through a patient's mouth. A housing 24 of the capsule is about the size of a large vitamin pill, e.g., about 15 mm long by 7 mm in diameter and comprises a plastic material that is biocompatible and not affected by stomach acid or other biological fluids. Tether 22 is extremely flexible and is relatively small in diameter, e.g., about 1 mm. Within housing 24, capsule 20 includes an actuator 28 that drivingly moves a scanner 26 to scan an inner surface of the lumen within a field of view (FOV) 30. When used to determine if a patient has BE, capsule 20 will be drawn back past LES 16 so that FOV 30 encompasses region 18. An image of region 18 that is provided by scanner 26 can thus be evaluated to indicate whether the tissue on the inner surface of esophagus 14 has turned the darker pink color indicative of BE.

Figure 2:
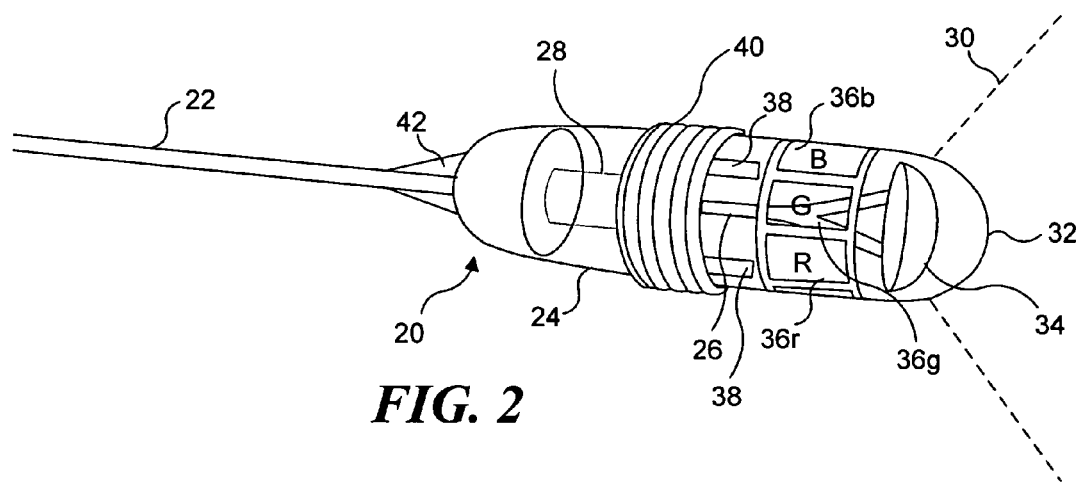
FIG. 2 is an enlarged isometric view of one embodiment of the present invention and indicating the relative wide field of view (FOV) provided by the scanner used therein.

FIG. 2 illustrates further details of this embodiment of capsule 20; a number of other embodiments of the capsule useful in the present invention are discussed below. A forward or distal end 32 of housing 24 is optically transparent, so that light emitted by a vibrating optical fiber comprising scanner 26 in this embodiment, can pass through an optical system 34 that includes a plurality of lenses, reaching the inner surface of the esophagus or other lumen in which capsule 20 is disposed. While the inner surface may be illuminated by scanner 26 using other wavebands of light, in this embodiment, the inner surface of the lumen is illuminated using white light. Light reflected from the inner surface is detected by a plurality of red, green, and blue (RGB) sensors 36r, 36g, and 36b, respectively. The white light that is used to illuminate the inner surface of the esophagus or lumen is conveyed to scanner 26 through an optical fiber (not separately shown) disposed within tether 22. The signals produced by the plurality of RGB sensors are conveyed back through electrical leads (not shown) within tether 22 for processing to produce an image corresponding to the portion of the inner surface that was scanned.

This embodiment also includes position sensors 38, which respond to an external signal provided by a signal source (not shown) external to the body of the patient, by producing a signal indicative of a location, and optionally, an orientation of capsule 20 within the patient's body. A suitable position sensor, which responds to electromagnetic signals, is available, for example, from Ascension Technology. Position sensors 38 can respond to an electromagnetic field, an RF signal, a light signal of a wavelength selected to penetrate tissue and pass into the lumen, or another appropriate signal. Alternatively, it is also contemplated that position sensors 38 can be replaced by a signal source, which is used in connection with an external sensor (not shown) to determine the location, and optionally, the orientation of capsule 20 within a patient's body. The external signal source or position sensor can be disposed at a specific location on the body of a patient to provide a reference, by strapping the signal source or position sensor to a patient's torso at the specific location.

A chemical sensor 40 is optionally included to sense a chemical parameter. For example, chemical sensor 40 can detect hydrogen ion concentration, i.e., pH, within the lumen. Alternatively or additionally, the chemical sensor can include a temperature sensor for monitoring an internal temperature of the lumen. Similarly, a pressure sensor can be employed in addition to or in place of chemical sensor 40, which is thus intended to represent any one or all of these sensors.

As a further option, a selectively releasable connection 42 can be provided to pneumatically or electrically disconnect the capsule from the tether when desired. When thus released from its connection with the tether, the capsule will be conveyed through the body lumen and if the lumen is involved with the digestive tract, the capsule will pass through and be expelled. The releasable connection can be activated with a pressurized pulse that is propagated through a passage in tether 22 from an external source (not shown), or can be an electrical signal that magnetically actuates releasable connection 42 using an electrical current provided through a lead in the tether. A similar releasable joint might also or alternatively be provided near the proximal end of the tether, to release the tether and capsule to pass on through the lumen together.

System Processing Overview

Figure 3:
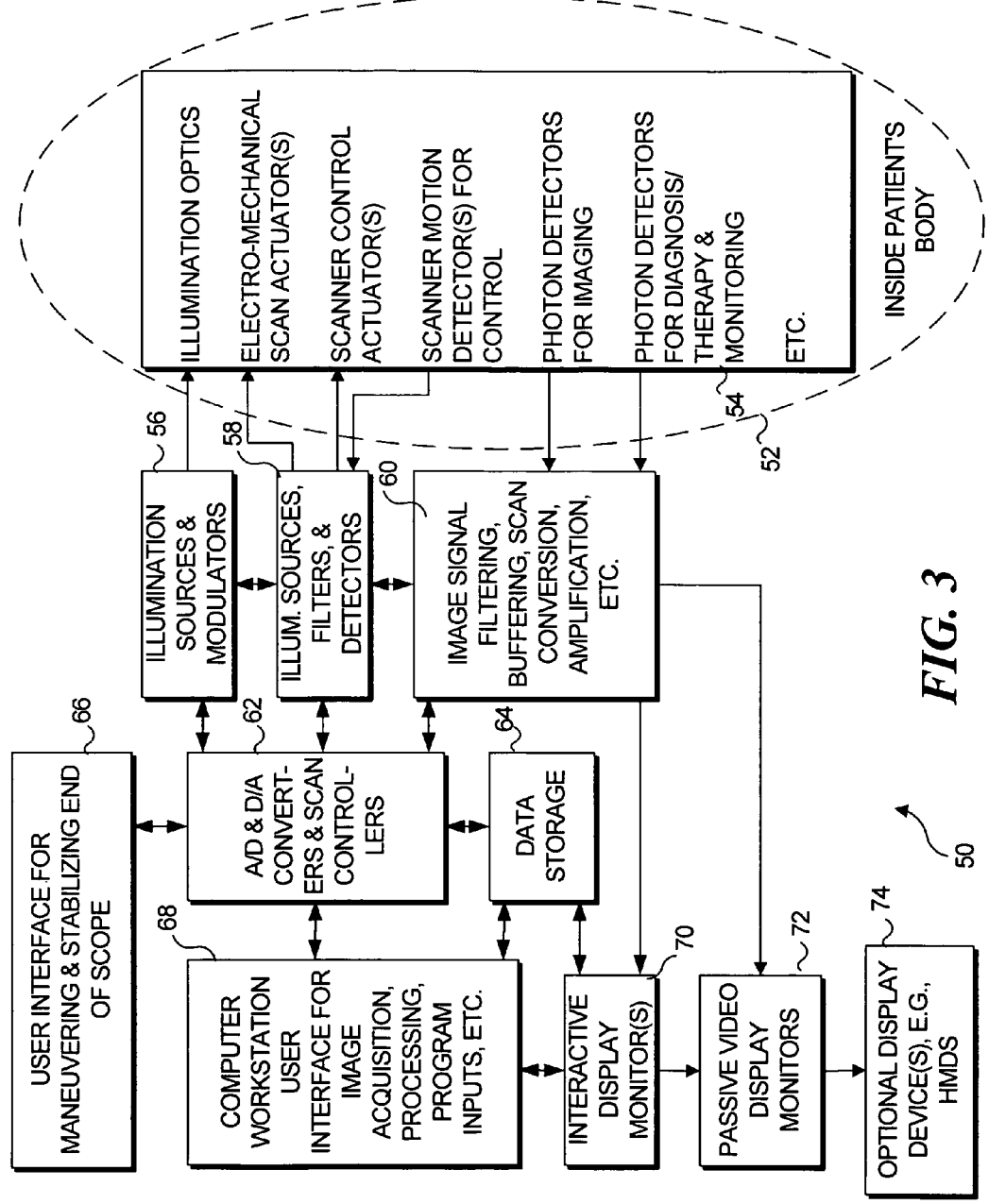
FIG. 3 is a block diagram illustrating the functional flow of signals in a scanning system in accord with the present invention, which is usable for monitoring, rendering diagnoses, and providing therapy to an inner surface of a lumen in a patient's body.

FIG. 3 illustrates a system 50, with external instrumentation, for processing the signals produced by various components that are inside the capsule and indicates how signals used for controlling the system are input to these components. In order to provide integrated imaging and other functionality, system 50 is thus divided into those components that remain external to the patient's body, and those which are in the capsule (i.e., the components within a dash line 52, some of which are optional depending upon the application in which this invention is being used). A block 54 thus lists the functional components that can be disposed within the capsule. As indicated in the Figure, these components include illumination optics, one or more electromechanical scan actuator(s), one or more scanner control actuator(s), one or more scanner motion detector(s) for control of the scanner motion, photon detectors for imaging a region of interest (ROI) (these photon detectors can alternatively be disposed externally if a light path is provided in the tether to convey the light reflected from the inner surface of the lumen to external detectors), and optionally, additional photon detectors for diagnostic purposes and for therapy and monitoring purposes (which can also be disposed externally of the capsule and patient). It should be noted that in regard to system 50, only the functional components actually required for a specific application, such as imaging an esophagus, may be included. Also, the additional functions besides imaging can be diagnostic, or therapy, or a combination of these functions, and can include taking a biopsy of tissue at an internal site for subsequent evaluation by carrying out an appropriate laboratory procedure. Although a specific embodiment of the capsule is not shown that includes a plurality of actuators, each associated with a different scanner, it will be apparent that due to the relatively small size of the scanners disclosed herein, it is possible to provide an array of such scanners to increase the total area scanned. Each such scanner will be provided with its own actuators and either with detectors to detect light from the region scanned by that scanner or with a waveguide to convey the light to one or more external detectors.

Externally, the illumination optics are supplied light from illumination sources and modulators, as shown in a block 56. Further details concerning several preferred embodiments of external light source systems for producing RGB, UV, IR, and/or high intensity light conveyed to the distal end of an optical fiber system are disclosed below. A block 58 indicates that illumination sources, modulators, filters, and detectors are optionally coupled to the electromechanical scan actuator(s) within the capsule, and/or to the scanner control actuators provided in the capsule. Scanner motion detectors are optionally used for controlling the scanning and produce a signal that is fed back to the scanner actuators, illumination source, and modulators to implement more accurate scanning control, if needed.

In a block 60, image signal filtering, buffering, scan conversion, amplification, and other processing functions are implemented using the electronic signals produced by the imaging photon detectors and for the other photon detectors employed for diagnosis/therapy, and monitoring purposes. Blocks 56, 58, and 60 are interconnected bi-directionally to convey signals that facilitate the functions performed by each respective block. Similarly, each of these blocks is bi-directionally coupled in communication with a block 62 in which analog-to-digital (A/D) and digital-to-analog (D/A) converters are provided for processing signals that are supplied to a computer workstation user interface employed for image acquisition, processing, for executing related programs, and for other functions. The computer workstation can be employed for mass screening of the population when programmed to process images produced by scanning inside an esophagus to detect Barrett's Esophagus so that near real-time results are provided and normally, without requiring a physician's evaluation.

Control signals from the computer workstation are fed back to block 62 and converted into analog signals, where appropriate, for controlling or actuating each of the functions provided in blocks 56, 58, and 60. The A/D converters and D/A converters within block 62 are also coupled bi-directionally to a block 64 in which data storage is provided, and to a block 66. Block 66 represents a user interface for maneuvering, positioning, and stabilizing the capsule with the scanner inside a lumen within a patient's body. Further description of a technique for determining a location of a capsule in a lumen and for stabilizing the capsule in the lumen are discussed below.

In block 64, the data storage is used for storing the image data produced by the detectors within a patient's body, and for storing other data related to the imaging and functions implemented by the scanner in the capsule. Block 64 is also coupled bi-directionally to the computer workstation and to interactive display monitor(s) in a block 70. Block 70 receives an input from block 60, enabling images of the ROI on the inner surface of the lumen to be displayed interactively. In addition, one or more passive video display monitors may be included within the system, as indicated in a block 72. Other types of display devices, for example, a head-mounted display (HMD) system, can also be provided, enabling medical personnel to view an ROI in a lumen as a pseudo-stereo image.

Figure 4:
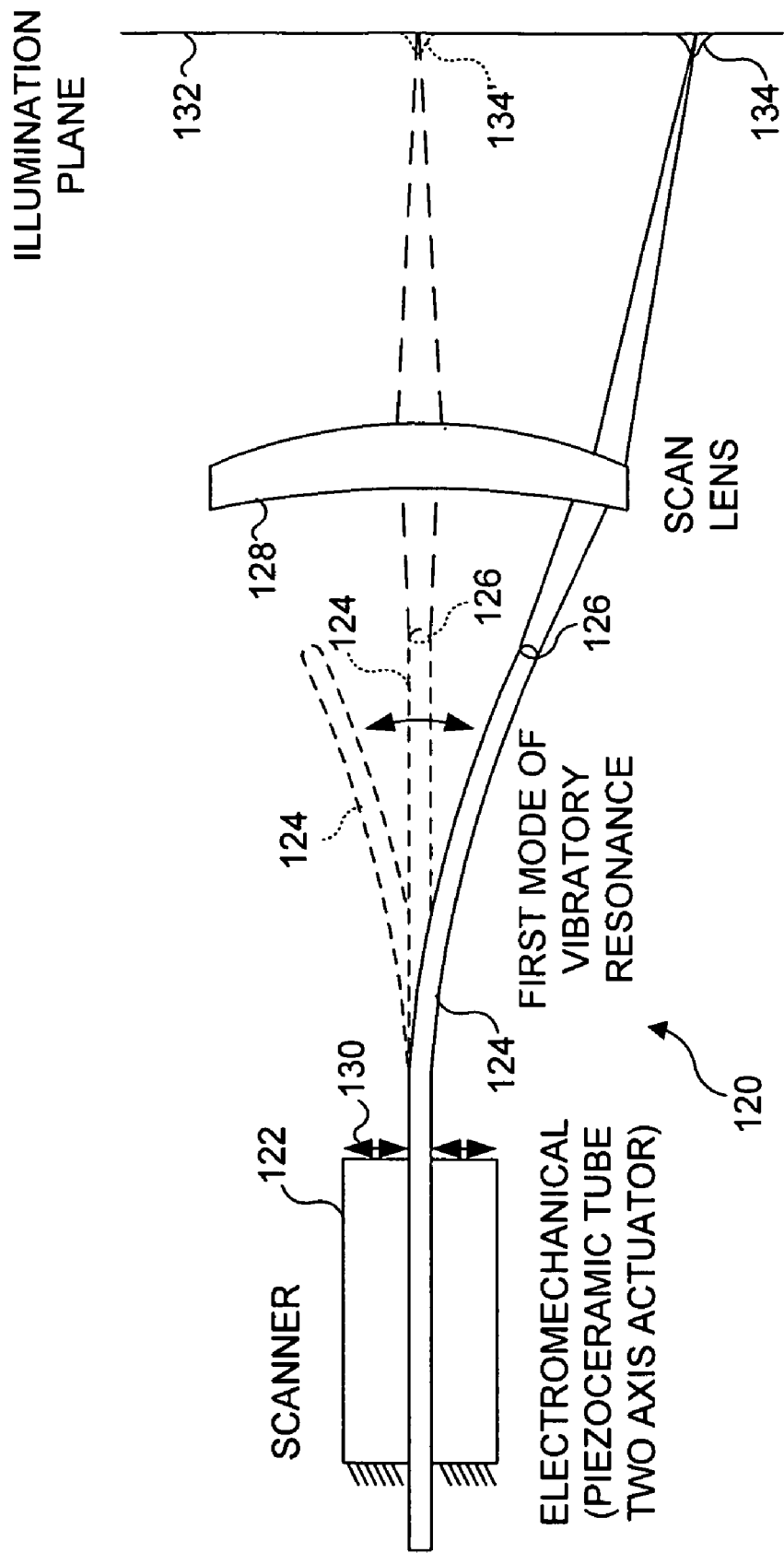
FIG. 4 illustrates a scanner embodiment having an actuator for driving a scanning optical fiber with a microlens, for use as an optical beam scanner with a scan lens, in connection with the present invention.

FIG. 4 illustrates one embodiment of a scanner 120 that can be used in the capsule. Scanner 120 includes an electromechanical device or piezo-ceramic tube actuator 122 that causes a first mode of vibratory resonance in a cantilevered optical fiber 124. In this embodiment, the cantilevered optical fiber includes a collimating lens 126 at its distal end and a scan lens 128 that directly focuses the optical beam of light that has passed through the collimating lens, onto an illumination plane 132, which typically would comprises a region on the inner surface of a lumen. Light focused by scan lens 128 forms a point spread function (PSF) 134 on illumination plane 132 and as the cantilevered optical fiber moves, a PSF 134' moves over the illumination plane. Although cantilevered optical fiber 124 can be limited to scanning along a single axis as indicated by arrows 130, it is typically preferable to use an actuator that moves the optical fiber so that it scans two-dimensionally, e.g., in a spiral pattern. However, at a high amplitude resonance vibration produced by a linear single axis actuator, the resulting motion of the optical fiber can be in two dimensions (2D) due to nonlinear cross-coupling of mechanical forces. Thus, two axis actuators are not required for 2D scanning.

Figure 5:
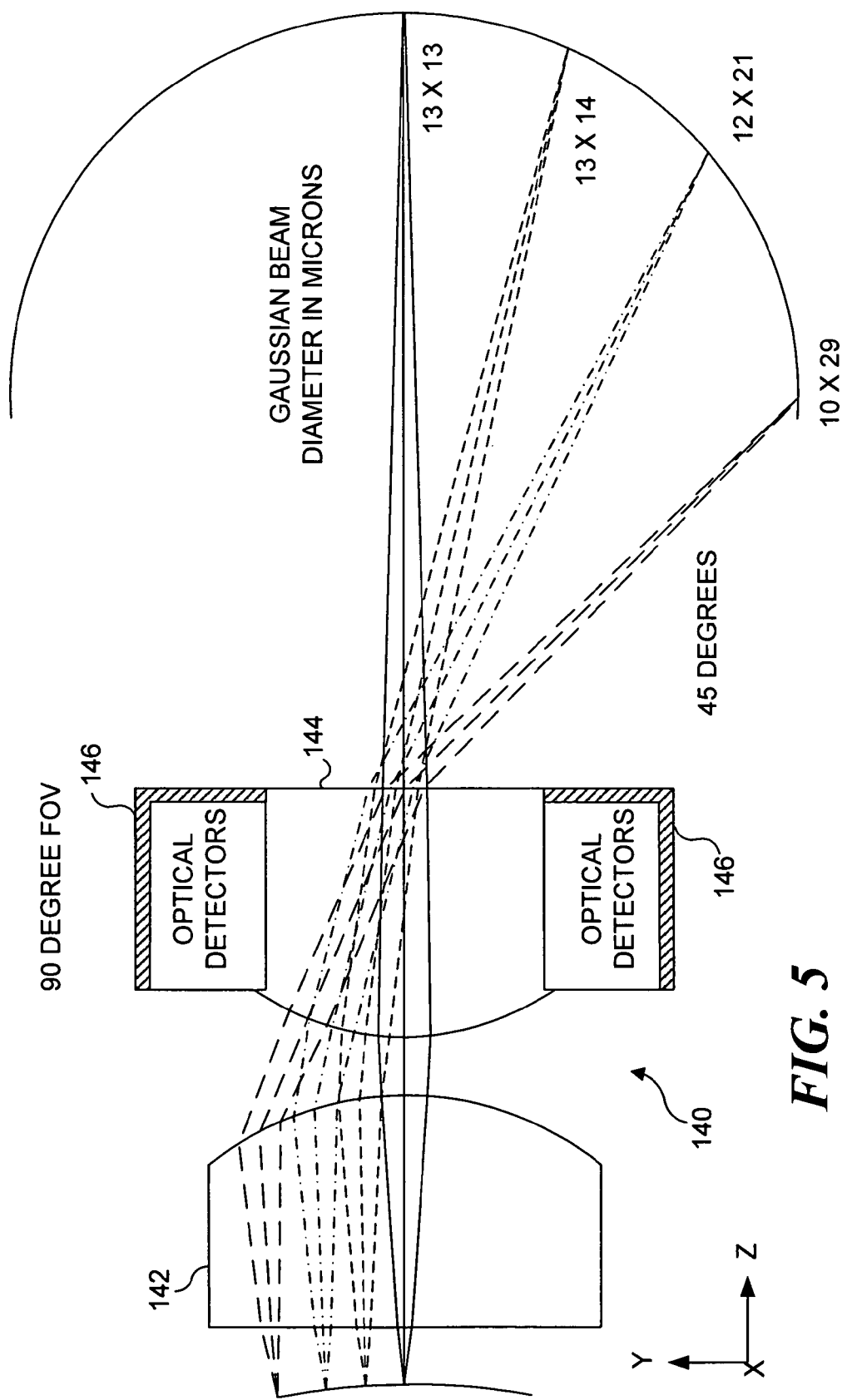
FIG. 5 is a schematic view of a point-source imaging embodiment, illustrating the variations in the imaged spot diameter at different scanning angles, in connection with a scanner used in the present invention.

FIG. 5 graphically illustrates an advantage of the scanners used in the present invention. Such fiberoptic scanners are readily capable of achieving a 90° FOV by imaging the scanned point-source object plane to a magnified image plane, which typically would comprise a region on the inner surface of a lumen. In contrast to FIG. 4, which illustrates optical beam scanning, FIG. 5 depicts a preferred embodiment of point source imaging that uses imaging lenses rather than the combination of a microlens and a scan lens. FIG. 5 illustrates the relative Gaussian beam diameters of the light used for illumination, at different angles between zero and 45°, i.e., over one-half of the total FOV, for one embodiment of an optical system 140 that includes lenses 142 and 144. In this embodiment, detection of reflected light is carried out using optical detector 146 that is disposed on and around the outer periphery of lens 144 (this portion of the lens does not transmit the illumination light), or alternatively, light reflected from the region being scanned can be collected and conveyed to external detectors (not shown). While shown in cross-section, it will be understood that optical detector 146 wraps around the entire periphery of lens 144 and actively detects light both on its forward surface and on all sides, as indicated by the hatched light sensing portions thereof.

Figure 6A:
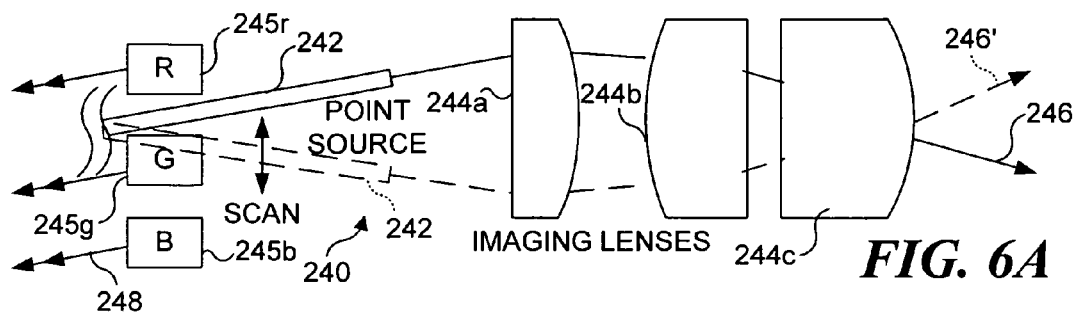
FIG. 6A is a schematic view of a scanning point-source illuminator with time-series photon detectors and imaging lenses for use in a scanner of the present invention.
Figure 6B:
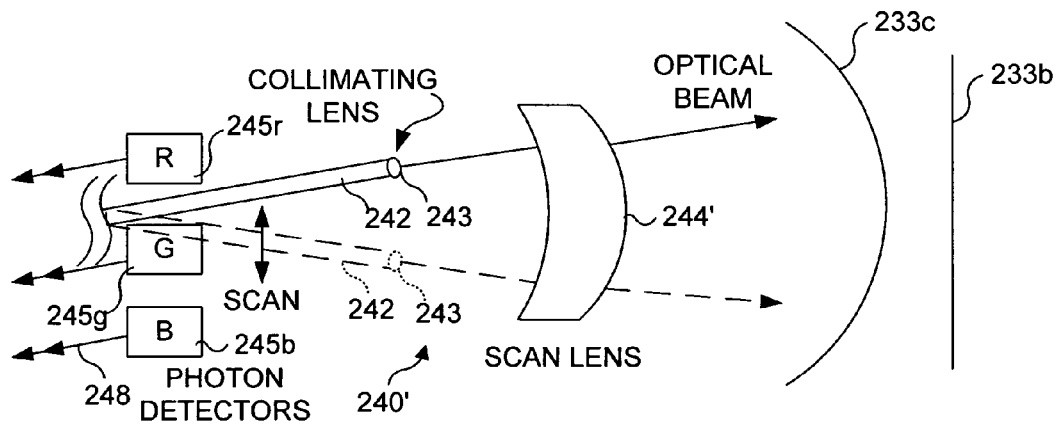
FIG. 6B is a schematic view of a scanning optical beam illuminator with a scan lens and detectors, for use in a scanner of the present invention.

FIGS. 6A and 6B illustrate embodiments of 2D scanning point-source illuminator 240 and optical beam illuminator 240' for use in the capsule of the present invention. In FIG. 6A, point-source illuminator 240 has the capability of providing a point source illumination through an optical fiber 242 within a capsule that is caused to scan an ROI on the inner surface of a lumen within a patient's body. Light emitted by the scanning optical fiber is transmitted through imaging lenses 244a, 244b, and 244c to illuminate different portions of the ROI as the point source provided by the scanning optical fiber is caused to move in a desired pattern within the capsule (not shown). In the position illustrated with solid lines, a light beam 246 illuminates a particular portion of the ROI, while in the position illustrated by dash lines, the scanning optical fiber produces light beam 246' that illuminates a different portion of the ROI. Light reflected from each successive point illuminated by the scanning optical fiber is reflected back through imaging lenses 244c, 244b, and 244a and is received by RGB photon detectors 245r, 245g, and 245b, respectively, which produce corresponding electrical signals that are transmitted outside the patient's body for use in displaying a full color image of the ROI. Alternatively, the light can be conveyed through the tether to external photon detectors disposed outside the patient's body.

In addition, therapy can be rendered to the inner surface of a lumen using scanning optical fiber 242. For example, by illuminating the points scanned by it using a relatively high powered laser, high intensity light for the purposes of drug activation or photodynamic therapy (PDT), or thermotherapy can be applied to the ROI. Since the signals produced by the RGB photon detectors correspond to successive points in the ROI, the image resulting from the signal that they produce is based upon a time series accumulation of image pixel data. Scanning optical fiber 242 is preferably a single mode or hollow optical fiber, of telecommunications grade or better. One significant advantage of this integrated system is that the mechanisms employed for generating the visual image are the same used for diagnostic, therapeutic, and surgical procedures. The directed optical illumination employed for image acquisition enables the most sophisticated diagnoses and therapies to be integrated into this single imaging system within a capsule sized to pass through a body lumen, (by sharing the scan engine, display, and user interface).

FIG. 6B illustrates a scanning optical beam illuminator 240' for use in a capsule (not shown) and which also includes scanning optical fiber 242, just as the embodiment shown in FIG. 6A. However, instead of using imaging lenses, scanning optical beam illuminator 240' employs a collimating lens 243 that is attached to the distal end of the scanning optical fiber and a scan lens 244'. The light conveyed through optical fiber 242 as it moves within the capsule is collimated by collimating lens 243 and then focused onto a flat illumination plane 233b, or a curved illumination plane 233c, corresponding to the ROI on the inner surface of a lumen within a patient's body. Light reflected from each successive point that is scanned as the scanning optical fiber moves passes back through scan lens 244' and is detected by RGB photon detectors 245r, 245g, and 245b, which respectively provide the RGB signals over lines 248 that are used to produce an image, with data accumulated pixel-by-pixel.

At the illumination plane, the beam of optical radiation is focused to achieve maximum intensity and/or optical quality, which is the goal for all modes of scanning. When tissue is coincident with the illumination plane, the optical irradiance is a function of the optical power and size of the light spot on the tissue. Thus, with regard to imaging, diagnoses, and therapy, the resolution of the scanner disposed in the capsule is determined by this spot size at the image plane and may also be limited by the sampling density (i.e., samples per unit area of tissue), since higher resolutions is achieved by providing more scan lines per area. With regard to image acquisition, the image resolution is determined by the illumination spot size, detector bandwidth (and scan rate), and signal-to-noise ratio (illumination intensity and collection efficiency), while image resolution is not limited by the physical size or number of the photon detectors.

Since diagnoses and therapies require accurate spatial discrimination, there is a need for directed illumination that is pre-calibrated before delivery. By integrating the optical imaging with diagnostic and therapeutic scanning delivered in a capsule, a medical practitioner can easily see the spatial discrimination of the optical scanning by viewing the displayed image before proceeding to diagnostic or therapeutic applications within the lumen in which the capsule is disposed. Finally, the integration of computer image capture electronics and image processing software enables the image, diagnostic, and therapeutic data to be analyzed on a pixel-by-pixel basis. Since each pixel corresponds to the same area or volume of tissue, the single fiber integrated system maintains spatial registration for all three functions, imaging, diagnosis, and therapy. Consistent spatial registration from the same point of view for all three functions makes the single optical fiber scanning system, delivered within a capsule passing through a lumen, highly accurate and easy to use by medical practitioners.

The advantages afforded by using the scanning device integrated within a relatively small capsule are:
Smaller size with integration;
Little or no sedation of the patient;
Physician is not required to insert the tethered capsule into a patient's esophagus;
Lower cost with integration and use of low cost components;
Lower flexural rigidity to allow greater access within various lumens in the body;
Faster procedural times, especially if requiring reiterations of therapy;
Greater accuracy with integrated high-resolution imager and interactive display;
Additional features with scanning optical system, such as variable resolution (real-time zooming) and enhanced stereo effects (such as shading);
Additional functionality with integrated non-visible optical sources and detectors;
Lower risk to patient for infection from multiple tools or multiple insertions within a lumen;
Faster recovery times for patient with less healthy tissue damage; and
Able to be left inside the body for extended periods of time to monitor chronic diseases.

Figure 6C:
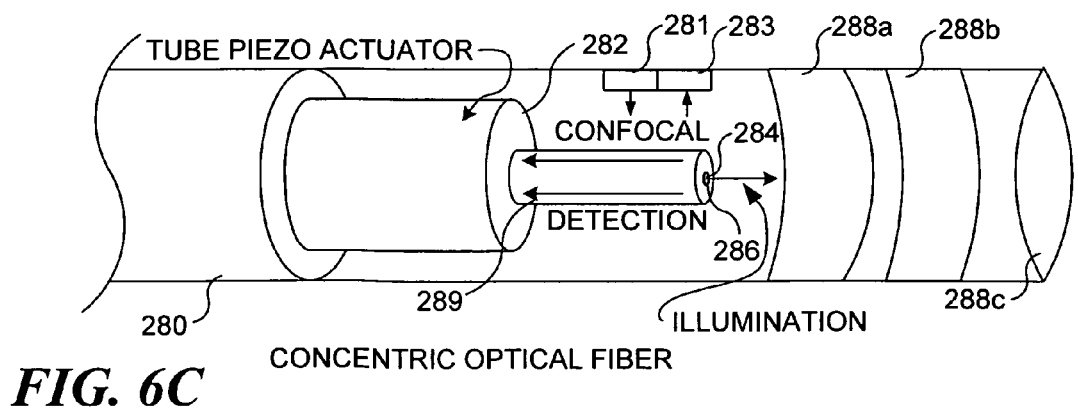
FIG. 6C is a schematic diagram showing a configuration for a scanner using a bundle of optical fibers and a single concentric core optical fiber.

FIG. 6C illustrates a portion of a concentric optical fiber assembly 280 for use as a confocal scanner that is readily employed with the capsule of the present invention. Optical fiber assembly 280 includes a relatively small central optical fiber 284, which is surrounded by cladding 286. A larger diameter optical fiber surrounds the smaller optical fiber. Illumination of an ROI is provided through small diameter optical fiber 284, and light emitted thereby passes through lenses 288a, 288b, and 288c to illuminate the ROI. Light reflected or otherwise received from the ROI is focused by these lenses back into an optical fiber assembly 289, which conveys the light that is received, through the tether, to instrumentation disposed outside the patient's body. It should be noted that a single optical fiber can both illuminate the ROI and convey light from the ROI to the external instrumentation in this so-called concentric confocal imaging. The concentric optical fiber geometry is a single mechanical unit either fused together upon heating pulling from a preform, or alternatively, the concentric regions of refractive index differences can be manufactured by doping the glass fiber radially. A tubular piezoelectric actuator 282 causes the concentric optical fibers to move together and thus to scan the ROI in one of the modes described above. The light collected in the surrounding optical fiber can be used with signals from detectors or optical fibers at radially increasing distances from the reflected confocal point to enhance image analysis and refine the depth of light penetration for diagnosis, imaging, and therapy. In extremely high-gain or discrimination detection configurations, the backscattered light may be collected in the same part of the waveguide (e.g., the core of the optical fiber). Such applications will use the optical coherence property to amplify the small signal level, producing diagnostic maps based upon optical coherence reflectometry (OCR) or optical coherence tomography (OCT), or laser-induced feedback.

FIGS. 6D and 6E illustrate an embodiment of a scanner useful within the capsule of the present invention, which includes detectors for RGB, ultraviolet (UV), and infrared (IR) spectral components. An optical fiber assembly 295 includes an internal actuator 291 mounted on a support 293 within the capsule (not shown). An optical fiber 300 enclosed within the housing having an opening 298 extends distally of actuator 291 and is moved by the internal actuator, which is preferably a tubular piezoelectric type, so as to achieve a desired scanning pattern, such as a helical or spiral scan. RGB detectors 292 and 294 are disposed above and below optical fiber 300, while RGB detectors 306 and 308 are disposed to the left and right of the optical fiber, as illustrated in FIG. 6E. In addition, RGB detectors 290 and 296 are disposed on the outer surface of the assembly on the top and bottom thereof, as indicated in these Figures. In a similar manner, RGB detectors 302 and 304 are mounted on the left and right sides of the detector as illustrated in FIG. 6E. UV detectors 310 and 312 are mounted on one of the diagonals between the RGB detectors, while IR detectors 314 and 316 are mounted on the other diagonal. Accordingly, a pseudo-stereo image can be produced in regard to the RGB, UV, or IR spectral components received by the various detectors included on this assembly, when imaging tissue on the inner surface of a lumen, from within the capsule of the present invention. By comparing signals from the multiple RGB detectors and knowing the orientation of the tethered capsule within the lumen, the level of the signal due to specular reflection and multiple scattering can be estimated and reduced by appropriate signal processing.

FIGS. 6F and 6G illustrate an optical fiber assembly 295' in which parallel and perpendicular polarized light detectors are included. Optical fiber 300 conveys light that is polarized in a parallel direction as indicated by reference numeral 328. On opposite sides of optical fiber 300 are disposed parallel polarized light detectors 334 and 336, while above and below optical fiber 300 are disposed perpendicular polarized light detectors 324 and 326, as shown in FIG. 6G. In addition, perpendicular polarized light detectors 320 and 322 are disposed above and below perpendicular polarized detectors 324 and 326, while parallel polarized light detectors 329 and 330 are disposed left and right of parallel polarized light detectors 334 and 336. Optical fiber assembly 295' is thus usable within a capsule to detect polarized light in both orientations, where the light is reflected or otherwise received from an ROI on the inner surface of a lumen, for analysis by instrumentation disposed external to the patient's body that receives the detector output signals through the tether that is coupled to the capsule (neither shown in these Figures). The signal produced by the various polarized light detectors can also be used for producing an image of the tissue inside the lumen, corresponding to that specific type of polarization, for display externally. By recording light that is shifted in polarization due to interaction with the tissue, specular reflection can be minimized. Since the degree of polarization from the tissue partially depends on tissue optical properties, various tissue types and depths can be discriminated by measuring both axes of polarization.

FIG. 7A illustrates a scanning and detection system 266 that is used with a capsule for providing both a pseudo-stereo image of an ROI on the inner surface of a lumen and for acquiring a spectral image that can be analyzed with a spectrophotometer externally of the lumen. In this system, an optical fiber assembly 250, which comprises the tether extending through the lumen and outside the patient's body includes an optical fiber 256 that is tapered at its distal end and is surrounded by a piezoelectric actuator 254. Actuator 254 causes optical fiber 256 to vibrate and scan an ROI, emitting light that passes through lenses 258a and 258b to illuminate the inner surface of the lumen (not shown). Light reflected from the ROI from this tissue or light otherwise received therefrom (such as phosphorescent or fluorescent emissions) is collected by twelve optical fibers 252 that are arranged in a circumferential array around optical fiber 256. As illustrated in this exemplary embodiment, optical fibers 1, 2, and 3, which are collectively referred to by a reference number 260, are respectively coupled through the tether to external RGB imaging detectors corresponding to a left side of the circumferential array. Similarly, optical fibers 7, 8, and 9, which are collectively identified by a reference number 262, are respectively coupled through the tether to external RGB imaging detectors for the right side of the circumferential array. Another set of optical fibers 264 corresponding to optical fibers that are coupled through the tether to a spectrophotometer 270. The spectrophotometer is employed for spectral analyses and spectral image acquisition using UV, visible, and/or IR light. Since the RGB detectors for the left and right side of the circumferential array receive light from the ROI at two spaced-apart portions of the array (i.e., the left and right sides), they produce a pseudo-stereo full color image that is readily viewed using an HMD display (not shown).

A schematic diagram illustrating a light source system 340 for producing light of different spectral composition that is coupled through the tether and into an optical fiber 360 disposed within the capsule is illustrated in FIG. 7B. In this embodiment, a red light source 342, a green light source 344, a blue light source 346, and an UV light source 348 are each selectively coupled into optical fiber 360. Optical fiber 360 extends comprises the tether so that the distal end of the optical fiber emits light to illuminate tissue on the inner surface of a lumen through which a capsule that includes the distal end of the optical fiber is passing. Attenuators 350 are provided at the proximal end of the optical fiber for each of the light sources so that the intensity of the light they produce can be selectively controlled. Three dichroic mirrors 352, 354, and 356 that include coatings specific to the color of light emitted by each of the corresponding green, blue, and UV light sources are positioned within the light path to reflect green, blue, and UV light, respectively, into the proximal end of optical fiber 360. Light that is outside the reflectance waveband for each of these dichroic mirrors is passed through the dichroic mirror and is focused by a lens 358 into the proximal end of optical fiber 360.

An alternative light source system 362 for use with the present invention is illustrated in FIG. 7C. In this embodiment, red, green, and blue light sources 342, 344, and 346, respectively, are coupled through optional attenuators 350 to a series or sequence of optical couplers 366 through lenses 364. Lenses 364 focus the light from each of the different colored light sources into optical fibers 365, which convey the light to optical couplers 366. In addition, an IR source 368 transmits light through an optional attenuator 350 and a lens 364 into optical fiber 365, which conveys the IR light to the last optical coupler in the sequence. Optical detectors 369 are provided for monitoring the light intensity levels or power levels for each of the different sources of light, enabling the intensity of the various light sources to be controlled. From the last optical coupler, an optical fiber 367 conveys light to an input to optical detectors 369, while the output from the last optical coupler is input to the proximal end of optical fiber 360 for input through to the scanner disposed within a capsule in a lumen inside a patient's body (neither the tether comprising optical fiber 360 or the capsule are shown—to simplify this drawing).

As indicated above, it is desirable to produce a scanning device with a small cross-sectional area that can be produced at relatively low cost and high volume to ensure that the endoscopic capsule scanning system is economical and thereby facilitate its widespread use. Micro-electromechanical systems (MEMS) technology using an integrated thin film device may be beneficially employed when producing economical scanners to more readily achieve this goal. FIGS. 8A, 8B, and 8C illustrate a thin film optical system 370 that can be adapted for use as a scanner within a capsule, in accord with the present invention. A further alternative 370' illustrated in FIG. 8D includes parallel cantilevered thin film optical waveguides for scanning and detectors.

In this thin film embodiment of a scanner that is useful in the present invention, electrostatic actuators 386 act on a thin film optical waveguide 380, which is supported on a raised ledge 378. The thin film optical waveguide is only about 0.003 mm in diameter. A distal portion 382 of the thin film optical waveguide is caused to scan in the two orthogonal directions indicated by the curved arrows in FIGS. 8A and 8B. It should be noted that the scanning motion can be one-dimensional (i.e., along a single axis), or as shown, in two dimensions (e.g., along a raster pattern or a spiral pattern). Optionally, the thin film optical device can be mounted in the capsule on a rod 373, which is then manually or mechanically rotated or vibrated to change the orientation or displace the single axis scan. Also provided is a lens 384 that is preferably mounted to a silicon substrate 376 (or other substrate material). As an alternative, actuators (not shown), which are external to the substrate but still disposed in the capsule, can be used instead of the electrostatic actuators, in which case, an optical fiber 374 and lens 384 would be supported by silicon substrate 376. The optical fiber would be caused to vibrate by the external actuators, causing the cantilevered thin film optical waveguide to resonantly scan.

Optical fiber 374 is preferably affixed to silicon substrate 376 within a centering V notch 390 to ensure that it is aligned with thin film optical waveguide 380. Since the optical fiber is approximately 0.1 mm in diameter, care must be taken to provide accurate alignment between the ends of the optical fiber and the thin film optical waveguide. FIGS. 8A and 8B show the embodiment using butt-end coupling between optical fiber 374 and a thin film optical waveguide 380. To ensure appropriate alignment between the optical fiber and the thin film optical waveguide, V notch 390 precisely establishes a disposition of the optical fiber relative to the thin film optical waveguide. An index-matching gel 375 or fluid can be used to couple light from optical fiber 374 to thin film optical waveguide 380. To reduce the gap filled by index-matching gel 375, the tip of the optical fiber can be etched to form a taper. Further, the tip length and surface can be adjusted by $CO_2$ laser machining before affixation. Other embodiments of the MEMS scanner described below further alleviate alignment problems.

In the embodiments shown in FIGS. 8A, 8B, and 8C, light reflected back from a target in the ROI passes through lens 384 and is received by RGB detectors 392r, 392g, and 3926b, respectively. These detectors, disposed in the capsule, respond to the light of the corresponding color, producing a signal that is conveyed proximally to the external components, as discussed above. In FIG. 8D, separate image and diagnostic/therapeutic thin film optical waveguides are spaced apart and scanned in parallel; this embodiment uses a diagnostic "DIAG" detector 392d.

Automated System for Mass Screening

One of the contemplated uses of the present invention is that it might eventually enable a nearly automated esophageal screening process to be carried out by a medical practitioner (and normally not by a medical doctor) to screen a patient for BE. FIG. 9 illustrates an automated system for use in connection with the present invention for conducting scanning of the inner surface of the esophagus of a patient 395 by a medical practitioner 408, to determine if the patient is afflicted with BE (or some other condition of the esophagus). This system includes a computer processor 394, which carries out many of the functions discussed above in connection with FIG. 3 and discussed in further detail below.

A combined optical fiber and electrical lead cable 397 couples computer processor 394 to a reel 396 that is used for retracting or enabling advancement of a capsule, in accord with the present invention, within the esophagus of patient 395, as a handle 402 on the reel is rotated. Tether 22, which is retracted or allowed to advance in the esophagus with the capsule, extends between lips 404 and down the esophagus of the patient. The tether is connected to combined optical fiber and electrical lead 397 at reel 402 and includes one or more optical fibers and one or more electrical leads that convey optical and electrical signals to and from the scanner disposed in the capsule (neither shown in this view). Patient 395 initially is provided glass 406 of liquid, such as water, to facilitate swallowing the capsule with its attached tether 22. The liquid is swallowed after the capsule is inserted into the patient's mouth and helps to advance the capsule through the esophagus with the normal peristalsis of the muscles comprising the walls of the esophagus as the patient swallows the liquid.

The capsule is allowed to advance into the stomach of the patient and is then withdrawn past the LES by medical practitioner 408 grasping handle 402 and rotating reel 396. Additionally, a computer-controlled withdrawal of the capsule is contemplated and will use a motorized reel to fully automate the screening process. Thus, the computer will determine how fast to withdraw the capsule, in response to criteria that determine the quality and content of the images being scanned by the capsule in real time. In addition to controlling the speed of the withdrawal of the capsule, the computer can control the intensity of light provided for scanning and patient-specific variables, and can carry out automated image stitching to form panoramic images of the interior surface of a lumen. An example of currently available automated image stitching software is available, for example, from Matthew Brown as "AutoStitch," (see the URL regarding this software at http://www.cs.ubc.ca/~mbrown/autostitch/autostitch.html). Such images can be used in connection with image recognition software to determine the location of the LES and to automate the determination of whether a patient has BE or some other medical problem. Also, images automatically stitched together to form a full 360° panoramic view can be calibrated to form a ruler-like measure in pixels of the length of the capsule from the LES, as an alternative measure to define the location of the capsule in a patient's esophagus.

By viewing a display 398 that is coupled to computer processor 394, the medical practitioner can readily observe images of the stomach and then, as the reel rewinds the tether to retract the capsule above the LES, the medical practitioner can observe images of the inner surface of the esophagus on the display. An indicator 400b is displayed at one side of the display to show the relative speed and direction with which the capsule is moving through the esophagus.

Computer processor 394 can detect the LES based upon the changes in an image 399 and display a distance 400a of the capsule above the LES, and can be programmed to automatically evaluate the images of the portion of the inner surface of the esophagus immediately above the LES to determine if the patient has the characteristic dark pink color at that point, which is indicative of BE. The medical practitioner should only be required to operate the reel and assist the patient in initially swallowing the capsule, since the results of the image scanning process are thus automated to detect the condition of the esophagus in near real time, providing an immediate indication of whether the patient is afflicted with BE. The efficiency of such a system should thus enable mass screenings of the population to be conducted at minimal cost, so that esophageal cancer of which BE is often a precursor, can be avoided by early detection of BE.

Functional Block Diagrams

FIG. 10 illustrates at least some of the variety of functions that can be carried out with the present invention when the capsule is disposed within a lumen of a patient's body. Functions such as diagnosis, therapy, and monitoring are shown in blocks that are formed with dash lines, while solid lines are used for imaging functions of a system 410 that is implemented with the capsule and related components. As illustrated in this Figure, imaging lasers 412 produce light that is directed into a patient's body via the tether and directed by the scanner in the capsule, through imaging optics used with the scanning optical fiber that is disposed in the capsule. Furthermore, diagnostic, therapeutic, and monitoring lasers in a block 416 that can be controlled by a remote optical switch and attenuators in a block 418 produce coherent light conveyed through an optical coupling mechanism 420 to additional optical components 422 disposed inside the capsule for use within the lumen of a patient's body. RGB photon detectors 430 respond to light received from the ROI on the inner surface of the lumen, producing an electrical signal that is conveyed through electrical conductors within the tether or running along side it, to instrumentation disposed outside the patient's body. Alternatively, the RGB light can be conveyed through optical fibers within the tether to external photon detectors 426 outside the body, or to other types of optical detectors 424 that include, for example, photodiodes and related circuitry.

As indicated in a box 432, the system may include additional high or low power UV, and/or visible, and/or IR detectors associated with collection optical fibers for use by one or more spectrophotometers or spectrum analyzers. For example, spectrophotometers and spectrum analyzers indicated in a block 434 can receive light conveyed through light collection optical fibers and/or as signals conveyed over conductors as indicated in a block 436. The system may include additional photon detectors disposed inside the capsule within the patient's body as a further option. Signals are exchanged bi-directionally between block 432 and 434 and a computer processor (or workstation) and data acquisition component in a block 440. The computer processor can execute algorithms that provide for non-linear scanning patterns and control algorithms and also can be programmed to carry out intensity data acquisition, image mapping, panoramic image stitching, and storage of data. In addition, tasks including real-time filtering (e.g., correction for motion and scanner artifacts), real-time determination of ratios and background subtraction, deconvolution, pseudo-stereo enhancement, and processing of the signals produced by the various detectors are implemented by the computer processor. Signals provided by the computer processor are output to image display devices (such as shown in FIG. 9) and for data storage on non-volatile storage (not shown). The image display devices may include cathode ray tube, liquid crystal displays, and HMD devices or other types of stereographic displays, as noted in a block 442.

Since commercially available displays typically require rectilinear video format, any non-rectilinear optical scanning patterns must be stored in data buffers (memory) and converted to the standard raster scanning format for the display monitors, to make use of the many advantages of non-rectilinear scanning, (such as a simplified single actuator, cylindrical scanner size, and lower scanning rates) used for the one or more scanners in the capsule. This additional step in signal conditioning and remapping is technically trivial with programmable memory devices.

In addition, image analysis software for carrying out spectral and multivariate analysis and for locating and calculating the limits of regions of interest are carried out using the computer processor or other computing device. In regard to the ROI on the inner surface of the lumen, the computations may determine its distribution, boundary, volume, color, and optical density, and based upon the data collected from the ROI, can determine a tissue disease state such as Barrett's Esophagus, medical staging, as well as calculate and monitor therapeutic dosage. All of these functions are indicated in a block 444, which may use the normal imaging computer processor of block 440. Block 444 is coupled to a block 446, in which additional interactive displays and image overlay formats are provided. Associated with block 444 is a block 448, which indicates that scanner power and control electronics are provided for actuating the electromechanical scanner and for receiving signals from servo sensors in a block 450, which are used for both normal image acquisition and enhancements involved in screening, monitoring, and diagnosis, as well as pixel accurate delivery of therapy to a desired site within the lumen.

Various embodiments of optical fiber scanning actuators have been described above, in connection with moving a scanner disposed in the capsule to image a ROI within a lumen. A block 454 indicates that provision is made for manual control of the distal tip of the scanning optical fiber, to enable the capsule containing the scanning optical fiber to be inserted into a patient's body and positioned at a desired location adjacent an ROI. The manual control will perhaps include turning the tether to rotate the capsule and scanner relative to the ROI in the lumen, and possibly automated servo sensors, as indicated in a block 456 to facilitate the positioning of the capsule and one or more scanners at the desired location. Once positioned, automatic vibration compensation for the scanner is provided, as noted in a block 452, to stabilize the image in regard to biological motion (breathing and cardiovascular movement) and physical movement of the patient. In addition, other mechanisms are provided in at least one embodiment for stabilizing the capsule where desired within the lumen of a patient's body.

Details of the various functions that can be implemented with the present invention are as follows:

Integrated Imaging, Screening, and Diagnosis

Optical tissue imaging using UV, visible, and IR wavelengths;
Fluorescence imaging using UV, visible, and IR wavelengths;
Thermal imaging using IR wavelengths;
Deep tissue imaging using IR wavelengths;
Concentric confocal and true confocal imaging;
Imaging through blood using IR wavelengths;
Polarization-contrast imaging;
Laser feedback microscopy;
Optical coherence tomography (OCT) and reflectometry (OCR);
Optically stimulated vibro-acoustography analysis;
High resolution and magnification tissue-contact imaging;
Laser-induced fluorescence (LIF) and ratio fluorescence imaging and detection;
Multi-photon excitation fluorescence imaging;
Fluorescence lifetime imaging and analysis;
True sizing of imaged structures using stereo and range finding options;
Laser-induced fluorescence spectroscopy (LIFS);
Raman spectroscopy analysis;
Elastic scattering spectroscopy (ESS) analysis;
Absorption spectroscopy;
Detection and mapping of chemi-luminescence and cell viability;
Spatial mapping of optical sensor data (oxygen concentrations, pH, ionic concentrations, etc.);
Temperature measurement and feedback control;
Guidance of pressure measurements (manometry) and correlation of visual and manometric observations of the esophagus, lower esophageal sphincter, stomach, pylorus, small intestine and other body lumens; and
Other measurements such as color, laser power delivery, tissue properties, photobleaching, and photocreation of compounds for monitoring and feedback control.

Therapies, Surgeries, and Monitoring

Photodynamic Therapy (PDT);
Heating of tissue and/or tumors, (e.g. hyperthermia treatment);
Laser surgery from optical illumination (UV, heat, and/or ablation)
Photoactivated chemistry, photopolymerization, and implantation of biomaterials;
Laser cauterization; and
Mechanical destruction of tissue using shock waves produced by absorption of pulsed optical radiation.

Interactive Displays & Advanced User Interface Design

Quasi-stereo on display monitors, stereographic mapping using pseudo color overlay, and true 3D display formats (Note: Individual display strategies and capabilities depend on the specific application); and
Interactive touch/point screen.

FIGS. 11A and 11B illustrate the different functions that can be carried out with the present invention, depending upon the instrumentation that is used. FIG. 11A shows a single scanning waveguide used for imaging, sampling diagnoses, and administering therapy, while in FIG. 11B, the single scanning waveguide is used for 3D imaging, obtaining a tissue biopsy, and monitoring endoscopic surgery. While in both these Figures, many of the components are identically provided, it is helpful to recognize that by making small modifications to the components that are used as part of the system, different functionality can be provided. In a system 460 shown in FIG. 11A, an interactive computer workstation monitor 462 enables medical practitioners to control the scanning optical fiber and to execute software algorithms used for imaging, diagnosis (e.g., optical biopsy), and administering therapy. A high resolution color monitor 464 receives signals from a scanning optical fiber 484 that are conveyed over an optical fiber system 488 to a distribution console 472. Optional RGB detectors may be provided if not included internally within the patient's body adjacent to scanning optical fiber 484. An ROI 486 is scanned by the optical fiber to produce the high resolution color images displayed to a user. In a passive display embodiment, two cathode ray tube monitors (CRTs) display images using two different contrast modes to generate the images of the same object (e.g., tissue). For example, the same resonant driven scanning optical fiber may produce both a full-color optical image on one CRT and a grayscale fluorescence image on the other CRT monitor. If the optical properties of the excitation and signal do not overlap, then two or more images may be generated simultaneously. Otherwise, the two images are either captured in a frame sequential method or in alternating line sweeps of the fast resonant scanner. To switch between image contrast modes (full-color optical and fluorescence), the light sources are shuttered or directly turned off/on. Synchronized in time during the modulation of both illumination power and spectral range, the signals from the photon detectors are recorded and displayed as separate images. In this example, having a second fluorescence image of the same ROI, a medical practitioner can find and positively identify small or pre-cancerous lesions that may or may not be visible on a standard white-light image.

It is contemplated that one of the two displays might be interactive, such as by using a touch screen monitor or interactive foot mouse or pedal that enables the medical practitioner to select (draw the outline) of an ROI for laser surgery. Since the image may be moving, the touch screen monitor will require the image to be captured and frozen in time. However, once this ROI is outlined, image segmentation and object recognition algorithms may be implemented to keep the ROI highlighted during real-time image acquisition and display. The interactive monitor can provide sidebar menus for the practitioner to set parameters for the laser therapies, such as power level and duration of laser radiation exposure. The second display would not be used interactively, but is preferably a high resolution monitor displaying the real-time optical image in full-color or grayscale. If IR photon detectors are integrated into the endoscope, the high resolution display with pseudo-color will allow the practitioner to monitor the progress of laser therapies, such as tissue heating and/or tissue irradiation in laser surgery.

The scanning optical fiber within the capsule is positioned at a desired location within the patient's body, opposite ROI 486, using the tether and an optional manual controller that facilitates tip navigation and stabilization, as indicated in a block 466. The disposition of the capsule within the lumen can be automatically determined based upon a position sensor signal or simply by monitoring the distance that the tether extends into the lumen, with reference to a scale provided on the tether, as discussed below in connection with FIG. 13. Within ROI 486, optical biopsy "spots" 485 illustrate the spatial and temporal distribution of single-point spectral measurements to diagnose for disease. These spots are distributed much like the current practice of invasively taking tissue samples for in vitro biopsy analysis. Each spot may be analyzed spectroscopically during a frame cycle of the optical scanner, separating $t_1$ and $t_2$ by, for example, about 1/30 second. In addition to the image provided by the scanning optical fiber, IR thermal photodetectors (and an optional temperature monitor) as indicated in a block 468 could be included for receiving IR signals from the ROI.

To facilitate control of the motion of the scanning optical fiber or light waveguide, electrical power for microsensors and control electronics are provided, as indicated in a block 470. The signals provided by the control electronics enable amplitude and displacement control of the optical fiber when the actuator that causes it to scan is controlled by both electrical hardware and software within block 470. A spectrophotometer and/or spectrum analyzer 474 is included for diagnostic purposes, since the spectral composition of light received from ROI 486 and distribution of optical biopsy spots 485 can be used for screening and diagnosis for such diseases as cancer by a medical practitioner evaluating the condition of the ROI in the lumen, based upon spectral photometric analysis. To illuminate the ROI so that it can be imaged, red, green, and blue light sources 476, 478, and 480 are combined and the light that they produce is conveyed through the optical fiber system to scanning optical fiber 484 within the capsule. The light source used for spectral analysis may be a high power pulse from one of the external RGB light sources (e.g., lasers), or a secondary laser or white light source. Since signal strength, time, and illumination intensity are limiting, a repeated single-point spectroscopic method will be initially employed, using flash illumination. In addition, the same or a different high power laser source 482 can be employed to administer therapy, such as PDT, the laser ablation of dysplasia, neoplasia, and tumors, and other types of therapy rendered with a high intensity source.

In using system 460, a medical practitioner navigates and maneuvers the flexible tether and attached capsule that includes the scanner, to an appropriate region of the lumen in a patient's body while watching the high resolution color monitor displaying the standard, full-color endoscopic image. The search for tumors, neoplasia, and/or pre-cancerous lesions in the lumen can begin by simply watching the monitor. A second monitor (not separately shown) included with spectrophotometer and spectrum analyzer 474 displays a fluorescence mapping in pseudo-color over a grayscale version of the image produced by the scanner in the capsule. When abnormal appearing tissue is found, the capsule is optionally mechanically stabilized (e.g., by inflating an attached balloon, as explained below). The ROI on the lumen wall is centered within the FOV of the scanner, then magnified using a multi-resolution capability provided by the scanner. The size of the ROI or cancer is estimated and a pixel boundary is determined by image processing either the visible image or the fluorescence image. If spectroscopic diagnosis is required, such as LIFS, the distribution of optical biopsy points is estimated along with illumination levels. The diagnostic measurements are performed by automatically delivering the illumination repeatedly over many imaging frames. The user can cease the diagnosis or have the workstation continue to improve signal-to-noise ratio and/or density of sampling until a clear diagnosis can be made from the images produced of the lumen inner surface by the scanner in the capsule. The results of diagnosis is expected to be in real-time and overlaid on top of the standard image.

If optical therapy is warranted, such as PDT, then an optical radiation exposure is determined and programmed into the interactive computer workstation controlling the scanner system in the capsule. The PDT treatment is an optical scan of high intensity laser illumination typically by high power laser source 482, pre-selected for the PDT fluorescent dye, and is controlled using dichroic filters, attenuators, and electromechanical shutters, as explained above. In a frame-sequential manner, both fluorescence images and visible images are acquired during PDT treatment rendered using the scanner in the capsule. The medical practitioner monitors the progress of the PDT treatment by observing these images acquired with the scanner, on both displays.

With reference to FIG. 11B, a scanning system 460' provided in a capsule is used for 3D imaging, biopsy, and monitoring endoscopic surgery of an inner surface of a lumen. To enable 3D imaging in a pseudo-stereo view of the ROI, an HMD 490 is included. In addition, the system includes high resolution color monitor 464, which was described above in connection with FIG. 11A. Also, an IR optical phase detector 492 is included for range finding within the lumen. High frequency modulation of IR illumination can be measured to determine phase shifts due to optical propagation distances on the order of a few millimeters. The distance between the distal end of the scanning optical fiber or light waveguide in the capsule and ROI 486 can be important in evaluating the intensity of light that should be applied during endoscopic surgery, for mapping a specific ROI 487 to determine its boundary or size, and for determining the size and shape of features such as the area of dysplasia or volume of a tumor comprising the ROI in the lumen. An UV-visible biopsy light source 494 enables an optical biopsy to be carried out at specific ROI 487. The spectrophotometer and spectrum analyzer in block 474 are useful in monitoring the status of the ROI during the endoscopic surgery being carried out, since the condition of the ROI during the endoscopic surgery can sometimes best be determined based upon the spectrum analysis provided by this instrumentation. In other respects, the components used for the alternative functions provided in FIGS. 11B are identical to those in FIG. 11A.

When using system 460', a medical practitioner again searches for neoplasia by moving the tether and capsule to reposition the scanner while watching high resolution color monitor 464, which shows the visible wavelength (full-color) image. When an ROI is found, the capsule can be mechanically stabilized, e.g., by inflating a balloon attached to it, as discussed below. Again, the ROI is centered within the FOV, and then magnified with the multi-resolution capability. However, if the surrounding tissue is moving so the acquired image is not stationary, a snapshot of the image is captured and transferred to the interactive computer workstation monitor, which is preferably an interactive display. The boundary of the stationary ROI is outlined on the interactive display screen, and an area of dysplasia or volume of the tumor is estimated from a diameter measurement in pixels and a distance measurement between the scanner and the tissue using IR optical phase detector 492 for range finding. An optical biopsy is taken with UV-visible biopsy light source 494, which can be an optical fiber-coupled arc lamp for elastic scattering spectroscopy (ESS). If warranted for this cancerous or pre-cancerous tissue, the optical radiation exposure is calculated, and a treatment protocol is programmed into interactive computer workstation monitor 462. Digital image processing algorithms can be calibrated for automatically segmenting the ROI or processing the scanner signal to eliminate motion artifacts from the acquired images in real-time, which may be equivalent or less than the display frame rate. The laser surgical treatment and/or cauterization can occur with high intensity laser 482 (IR) that is optically coupled with the visible optical scanner. If the IR range finding option is not required, but an IR temperature monitor or laser monitor is desired, then the IR source can instead be used for these alternative monitoring functions. In a frame-sequential manner, both the IR and visible images are acquired during the laser surgery and/or cauterization. The IR image is either a mapping of the back scatter from the laser illumination as it scans the ROI in the lumen or a thermal image of the ROI, which can be displayed on the interactive computer display as pseudo-color over a grayscale visible image. The medical practitioner monitors the progress of the IR radiation treatment by observing these acquired images on both the high resolution and interactive display monitors.

Determining Disposition of Capsule in Lumen

In many applications of the present invention, it'll be important to determine the location of the capsule within the lumen through which the capsule is moving. Several different techniques can be employed for making this determination, including the use of a position sensor within the capsule, which detects a signal from an external reference source, so that the disposition (and optionally, orientation) of the capsule relative to the reference source can be determined. Alternatively, a signal source can be included within the capsule for use with an external position sensor to determine the location (and optionally, orientation) of the capsule within a patient's body and thus, within a lumen of the patient's body. The inclusion of a position sensor within the capsule is discussed above.

As a further alternative, an electronic measuring device 500 can be provided for determining a length of tether 22 that has entered a patient's body within a lumen so that the nominal disposition of the capsule within the lumen is known. Electronic measuring device 500 is shown in FIGS. 12A and 12B. In these Figures, an electronic lead 502 is shown running adjacent to tether 22, but could alternatively be included internally within the tether. Electronic measuring device 500 includes a bit piece 504, which is shaped to be comfortably clamped between a patient's teeth, so that tether 22 passes into the patient's esophagus. Also included is a housing 506 within which are disposed a light emitter 508 and a light detector 512, spaced apart so that a notched encoder wheel 510 rotates between the light emitter and the light detector. Notched encoder wheel 510 is mounted on a shaft 514 that is rotatably turned by a wheel 516 in response to tether 22 moving. A tension wheel 518 applies a force against tether 22 to maintain the tether in contact with wheel 516. Wheel 516 and tension wheel 518 are supported by a bracket 520. In response to the notched encoder wheel rotating between light emitter 508 in light detector 512, the light detector produces a pulse signal indicative of the length of tether 22 that is within the esophagus (or other lumen) of a patient.

An even simpler approach for determining the length of tether 22 that is within a lumen, so as to determine a nominal position of a capsule within the lumen is illustrated in FIG. 13. Tether 22 has a plurality of spaced-apart ruled marks applied to its outer surface, to indicate the distance from the capsule along the tether. Accordingly, a user can simply read the distance from the capsule by reference to the marks on the tether, to determine the distance that the capsule has traveled into the lumen.

Use of Dual Cladding Optical Fiber

In the above discussion, it was noted that a dual cladding optical fiber could be employed for conveying light signals both distally to the capsule and proximally back to detectors disposed external to the patient's body. An exemplary embodiment of a dual cladding optical fiber 540 includes a very low refractive index, $n_{oc}$, outer cladding 542, which can be added to a readily available single mode optical fiber, or can be purchased as a custom optical fiber that already has the outer cladding applied. Outer cladding 542 surrounds a low refractive index ($n_{ic}$) inner cladding 544, which serves as a waveguide for light collected from the inner surface of a lumen by the capsule. A core 546 with a high refractive index, $n_c$, conveys light for illuminating the inner surface of the lumen and this light can be white, i.e., light have substantially equal intensity RGB components, or may comprise light of other wavelengths or wavebands. The relationship of the refractive indices of these components of the dual cladding optical fiber is thus as follows: $n_c > n_{ic} \gg n_{oc}$. Alternatively, outer cladding 542 can be formed as a thin metal film, e.g., of gold, aluminum, or silver. As yet a further alternative, outer cladding 542 can simply be air, or a composition comprising mostly air and an appropriate polymer.

Use of dual cladding optical fiber 540 simplifies the components required for a capsule 552, as shown in FIG. 15. For example, light detectors are not required in capsule 552. Further, since there is no need to convey electrical signals from light detectors within the capsule, a lead 550 that runs alongside dual cladding optical fiber 540 in the tether is only required for conveying an electrical signal to energize an actuator 560. Lead 550 is shown alongside dual cladding optical fiber 540 in FIG. 15, but internal to highly flexible and thin outer sheathing 564 of the tether for capsule 552. Preferably, the cantilevered section of dual cladding optical fiber 554 is scanned, emitting light that illuminates the inner surfaces of esophagus 14, as indicated by dash line 562. The optical system in capsule 552 includes a first lens 556 and a second lens 558 through which light emitted by moving optical fiber 554 is conveyed onto the inner surface of the lumen. Light reflected back from the inner surface of the lumen also passes through the optical system and enters inner cladding 544, which conveys the light externally of the lumen, to appropriate detectors, as discussed above.

Use of a Balloon Coupled to Capsule

FIG. 16 illustrates a capsule 570 that has an inflatable balloon 574 coupled to its proximal end. The balloon does not interfere with illuminating light 572 being directed from the distal end of the capsule to an inner surface 582 of the lumen in which the capsule is disposed. A volume 586 within balloon 574 is selectively inflated with fluid or air that is conveyed through a lumen 578 within a tether 576. The fluid exits lumen 578 through at least one opening 588 that is formed in the portion of the tether encompassed by the balloon.

The balloon can be inflated to serve one or more distinct purposes, as follows. For example, balloon 574 can be inflated so that peristaltic muscle tissue action advances the balloon and the capsule through the lumen; the larger diameter of the balloon enables the force applied by the muscle tissue to more efficiently advance the balloon and the connected capsule through the lumen. As a further option, the balloon, when inflated, can convey a pressure from a wall of a lumen in which the balloon is disposed, to a pressure sensor (not shown here—but discussed above) that is on the capsule or otherwise in fluid communication with interior volume 586, so that the pressure exerted by the lumen wall can be monitored externally of the lumen. The pressure can be determinative of various conditions or provide other information of interest.

Instead of enabling the capsule to advance, the balloon can be at least partially inflated to enlarge a cross-sectional size of the balloon, thereby preventing further movement of the capsule through a portion of a lumen or other passage having a cross-sectional size that is smaller than that of the balloon. Finally, the balloon can be inflated to generally center and stabilize the capsule within a lumen of the patient's body so that scanning of the inner surface of the lumen can be more effectively carried out.

Electrical Contacts to Stimulate Peristalsis

A capsule 590 is shown within a lumen 592 in FIG. 17 and includes a plurality of electrical contacts 594 disposed on the outer surface of the housing of the capsule. Electrical contacts 594 are connected to leads 598, which extend within a passage 602 formed in a tether 600. The leads are coupled to an electrical power source (not shown). An electrical voltage is thereby selectively applied to electrical contacts 594 through leads 598, causing muscle tissue 604 stimulating peristalsis in the muscle tissue of lumen 592, which advances the capsule through the lumen. Optionally, electrical contacts 596 that are connected to tether 600 proximal of capsule 590 can be employed in lieu of or in addition to electrical contacts 594 to stimulate peristalsis of the muscle tissue.

Mechanical Biopsy

FIG. 18 illustrates a capsule 620 that is coupled to a tether 624. Tether 624 includes an annular passage 622 within which one or more cytological brushes 626 or biopsy forceps (not shown) are controllably advanced to contact the inner surface of the lumen in which capsule 620 is disposed. Cytological brush 626 is advanced from annular passage 622 into contact with the tissue on the inner surface, so that cells of the tissue lining the lumen are transferred onto the bristles of the brush. The cytological brush is then withdrawn into the annular passage and after the capsule and tether are withdrawn from the lumen in the patient's body, the cell sample can be removed from the bristles for further processing and study. Although not shown, the annular passage can be used to pull back a flap on the capsule that exposes bristles that can be advanced from the capsule. Instead of an annular passage, the cytological brush, a fine needle, or other type of mechanical biopsy device can be advanced through a piggyback passage provided on the tether (not shown). A grasping device may also be employed in the annular or piggyback passage to gather a sample from the lumen and retract with the sample back into the passage. Such a passage can also be used as an intake for a fluid that is drawn through the passage to the proximal end of the tether that is outside the patient's body.

Multiple Images

As noted above, it is contemplated that a plurality of scanners can be included in the capsule, in accord with the present invention. Since each of the scanners are relatively small in size, they can be configured in a spaced-apart array that can image a large field of view, encompassing, for example, an entire 360° view of the inner surface of a lumen. Alternatively, as shown in FIG. 19, a single scanner can be used in a capsule 650, to image the four sides of a lumen 672 (including, the two sides shown, as well as the side behind the pyramidal mirror and the side opposite, neither of which is visible in this Figure). Capsule 650 is connected to a tether 652 that extends externally of lumen 672. A moving optical fiber 654 in the capsule emits light that is directed through a lens 656, toward a pyramidal-shaped mirror 658. The adjacent mirror surfaces of pyramidal mirror 658 reflect the light from lens 656 in the four different directions and through lenses 660a and 660b (the other two lenses not being shown). Light reflected from the inner surface of lumen 672 is detected by annular detectors 670a and 670b (the other two annular detectors not being shown). If the extent of overlap of the images provided on the four sides of capsule 650 is incomplete, a user can rotate tether 652, as indicated by an arrow 674, which will rotate capsule 650 to change the direction in which the scanning of the inner surface occurs, so that additional images can be produced and optionally connected together to form a full panoramic view of the inner surface of the lumen.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for imaging an inner surface of a lumen in a body, comprising:
    (a) a capsule housing that is sized to readily pass through the lumen, the capsule housing having at least an imaging portion that is optically transparent;
    (b) a light source;
    (c) a scanner disposed within the capsule housing and coupled to the light source, the scanner having an actuator that drives the scanner to scan an inner surface of a lumen in a body in a desired scanning pattern with a beam of light from the scanner;
    (d) at least one light sensor that responds to light that has been reflected from an inner surface of a lumen, producing an electrical signal that is indicative of an intensity of the light;
    (e) an optical system that focuses the light emitted from the scanner onto a portion of an inner surface of a lumen in a body; and
    (f) a flexible tether that is connected to the capsule housing and which extends proximally through a lumen to enable a force to be applied to the capsule housing to control a movement of the capsule housing, wherein the flexible tether is of sufficient strength to retract the capsule housing from the lumen but is too flexible to push the capsule housing distally through the lumen.

2. The apparatus of claim 1, wherein the at least one light sensor is disposed external to the capsule housing, the light reflected from an inner surface of a lumen being conveyed through an optically transmissive channel included within the tether to the at least one light sensor.

3. The apparatus of claim 2, wherein the optically transmissive channel comprises one of:

(a) a core of an optical fiber that comprises the tether;
(b) a core of an optical fiber that also conveys light from the light source through the tether and into the capsule housing; and
(c) a cladding of an optical fiber that comprises the tether.

4. The apparatus of claim 1, wherein the at least one light sensor is disposed within the capsule housing, the light reflected from an inner surface of a lumen being received by the at least one light sensor, causing a corresponding electrical signal to be produced.

5. The apparatus of claim 4, wherein the tether includes at least one electrical lead that is coupled to the light sensor and conveys the electrical signal from the at least one light sensor to a location that is outside of a lumen in a body.

6. The apparatus of claim 1, wherein the scanner includes a scanning mirror that is driven by the actuator to reflect the light produced by the light source, in the desired scanning pattern.

7. The apparatus of claim 1, wherein the scanner comprises a waveguide that is driven to move by the actuator, so that the waveguide emits light from a distal end of the waveguide, to scan in the desired pattern.

8. The apparatus of claim 1, further comprising a pressure sensor disposed on the capsule housing for monitoring a pressure applied to the capsule, the pressure sensor producing a pressure signal indicative of the pressure applied to the capsule housing.

9. The apparatus of claim 1, further comprising a location sensor for monitoring a location of the capsule housing within a lumen relative to a reference point.

10. The apparatus of claim 1, further comprising a chemical sensor for monitoring at least one chemical parameter from within a lumen of a body.

11. The apparatus of claim 1, further comprising means for performing a biopsy to take a tissue sample at a desired site within a lumen of a body.

12. The apparatus of claim 1, further comprising at least one electrical contact disposed on an exterior of the capsule housing, to stimulate a muscle in a wall of a lumen of a body in which the capsule housing is disposed, to promote peristalsis that moves the capsule housing through a lumen.

13. The apparatus of claim 1, wherein the tether includes a plurality of scale markings that serve to enable a user to measure a distance traveled by the capsule housing into a lumen of a body.

14. The apparatus of claim 1, further comprising a rotary component engaged by the tether that is rotated as the capsule housing moves through a lumen of a body, the rotary component being used to provide an indication of a distance traveled by the capsule housing into a lumen.

15. The apparatus of claim 14, wherein a lumen comprises an esophagus of a body, further comprising a bite bar that is adapted to be disposed in a mouth of a patient to support the rotary component, so as to ensure a reproducible tracking of the distance through which the capsule housing moves within an esophagus.

16. The apparatus of claim 14, further comprising a selectively releasable joint for connecting to the tether and disposed at least at one of:
(a) adjacent to the capsule housing; and
(b) adjacent to the bite bar.

17. The apparatus of claim 1, wherein the optics system includes at least one reflective surface for directing the light emitted from the scanner laterally to a side of the capsule is housing.

18. The apparatus of claim 1, wherein the optical system includes at least one lens disposed between the scanner and the imaging portion of the capsule.

19. The apparatus of claim 1, wherein the imaging portion of the capsule is disposed at a distal end of the capsule housing, the tether being connected to a proximal end of the capsule housing.

20. The apparatus of claim 1, wherein the optical system includes at least one filter that is disposed so as to filter light that is one of:
(a) produced by the scanner and directed to an internal surface of a lumen; and
(b) reflected from an internal surface of a lumen before the light is sensed by the at least one light sensor.

21. The apparatus of claim 1, wherein the scanner comprises one of:
(a) a single mode optical fiber;
(b) a dual cladding optical fiber;
(c) a single mode optical fiber used for conveying light from the light source, and at least one multimode collection optical fiber for conveying light reflected from an inner surface of a lumen to the at least one light sensor; and
(d) a waveguide comprising a microelectromechanical system (MEMS) device.

22. The apparatus of claim 1, wherein the scanner comprises one of a waveguide and an optical fiber that is driven by the actuator to move at about a resonant frequency when scanning in the desired pattern.

23. The apparatus of claim 22, further comprising a feedback sensor for controlling a movement of said one of the waveguide and the optical fiber, so as to substantially reduce any distortion in an image produced by scanning with the light beam produced by said one of the waveguide and the optical fiber.

24. The apparatus of claim 1, wherein the actuator comprises an electromechanical actuator that produces a driving force in a plurality of orthogonal directions, to achieve the desired pattern for scanning an internal surface of a lumen in a body.

25. The apparatus of claim 1, wherein the at least one light sensor comprises a plurality of light sensors, including light sensors that are responsive to at least one of:
(a) light of different spectral wavebands; and
(b) polarized light.

26. The apparatus of claim 1, wherein the optical system directs the light emitted by the scanner through the imaging portion of the capsule housing, so that the desired scanning pattern illuminates an interior surface of a lumen over substantially an entire 360 degree arc.

27. The apparatus of claim 1, further comprising a plurality of scanners disposed within the capsule housing, each scanner including a separate actuator and being configured to scan a different part of an inner surface of a lumen in a body.

28. The apparatus of claim 27, wherein the plurality of scanners are configured to at least:
(a) increase a field of view compared to a field of view provided by a single scanner;
(b) scan an inner surface of a lumen from opposite ends of the capsule housing;
(c) provide a stereo scan image of an inner surface of a lumen;
(d) perform a diagnostic scan of an inner surface of a lumen using light of a predefined waveband;
(e) provide a therapeutic scan of an inner surface of a lumen using light from at least one of the plurality of scanners;

(f) monitor a state of therapy being applied within a lumen; and (g) provide illumination used to measure distance between one scanner and an inner surface of a lumen.

29. The apparatus of claim 27, wherein the plurality of scanners are spaced apart in an array within the capsule housing, and wherein the optical system directs the light emitted from each scanner to different parts of an inner surface of a lumen.

30. The apparatus of claim 1, wherein the capsule housing is sized and configured to be swallowed by a patient with the tether connected thereto.

31. The apparatus of claim 1, further comprising a data recording medium that receives an electrical signal from the at least one light sensor and stores data corresponding to the electrical signal produced by the at least one light sensor.

32. The apparatus of claim 31, wherein the data represent a plurality of image frames that are readily combined to provide at least one continuous two-dimensional image of an inner surface of a lumen in a body.

33. The apparatus of claim 1, further comprising a spectral analyzer that analyzes an electrical signal produced by the at least one light sensor in a desired range that is selected from a waveband range extending from an ultraviolet to an infrared waveband.

34. The apparatus of claim 1, further comprising an inflatable balloon coupled to the capsule, the balloon being inflated to at least one of:
(a) enable peristaltic advancement of the balloon with the capsule through a lumen in a body by forces applied by a lumen on the balloon;
(b) convey a fluid pressure from a wall of a lumen in which the balloon is disposed, to a pressure sensor that enables a pressure exerted thereby on the balloon to be monitored;
(c) to enlarge a cross-sectional size of the balloon and the capsule housing in combination, thereby preventing further movement of the capsule housing through a cross-sectional passage in a body that is smaller than a cross-sectional size of the balloon when the balloon is at least partially inflated; and
(d) generally center the capsule housing within a lumen of a body.

35. The apparatus of claim 1, further comprising a disconnect that is selectively actuatable to release the capsule housing from the tether.

36. A capsular system for scanning an inner surface of a lumen in a body, comprising:
(a) a housing defining a capsule that is sized to fit within a lumen in a body and to be readily advanced therethrough;
(b) a flexible tether connected to the capsule and having a length sufficient to extend proximally external of a lumen in which the housing is disposed, wherein the flexible tether is of sufficient strength to retract the capsule from the lumen but is too flexible to push the capsule distally through the lumen;
(c) a light source that produces light for illuminating an inner surface of a lumen in which the housing is disposed;
(d) a scanner having an actuator that drives the scanner to scan an inner surface of a lumen in a body in a desired scanning pattern with a beam of light from the scanner; and
(e) a light sensor that receives light reflected from a region of an inner surface of a lumen, producing a signal indicative of an intensity thereof.

37. The capsular system of claim 36, wherein the housing is shaped to facilitate swallowing by a patient down an esophagus, the scanner being used to scan an inner surface of an esophagus to detect a visual change associated with Barrett's Esophagus.

38. The capsular system of claim 36, further comprising a location sensor disposed within the housing to determine a relative position of the housing within a lumen of a body, including a distance along a lumen traversed by the housing relative to a reference point.

39. The capsular system of claim 36, wherein the scanner comprises one of a waveguide and an optical fiber, a distal end of the waveguide being driven by the actuator to move and emit a beam of light in the desired pattern.

40. The capsular system of claim 36, wherein the scanner further includes an optical system having at least one lens disposed within the housing to modify the light emitted from the distal end of the waveguide so as to facilitate scanning a desired region of an inner surface of a lumen in which the housing is disposed.

41. The capsular system of claim 40, further comprising a plurality of scanners disposed within the housing, each scanner being directed to scan a different portion of an inner surface of a lumen in which the housing is disposed.

42. The capsular system of claim 36, wherein the light sensor is responsive to at least one of:
(a) white light;
(b) visible light within a specific waveband;
(c) non-visible light within a specific waveband; and
(d) polarized light.

43. A method for scanning an inner surface of a lumen in a body, comprising the steps of:
(a) introducing a capsule that includes a scanner into the lumen, the capsule further including a tether coupled to the capsule;
(b) enabling the capsule to advance through the lumen, with a proximal end of the tether remaining outside the lumen;
(c) controlling a disposition of the capsule within the lumen by exerting a force on the tether;
(d) producing an image of the inner surface of the lumen with the scanner; and
(e) reproducibly tracking a distance through which the capsule moves within the lumen.

44. The method of claim 43, wherein the step of controlling a disposition comprises the step of using the tether to position the capsule to scan a desired region in the lumen with the scanner.

45. The method of claim 43, wherein the step of enabling the capsule to advance comprises the step of enabling a peristaltic movement of muscle tissue comprising walls of the lumen to move the capsule through the lumen.

46. The method of claim 45, wherein the step of enabling the capsule to advance further comprises the step of inflating a balloon around the capsule so that the muscle tissue interacts with the balloon to advance the capsule through the lumen.

47. The method of claim 43, further comprising the step of exciting the muscle tissue with an electrical current applied through a conductor disposed on at least one of the capsule and the tether, the electrical current causing a peristaltic movement of muscle tissue so as to at least one of:
(a) advance the capsule through the lumen;
(b) change a portion of the inner surface of the lumen that is imaged with the scanner by causing relative movement between the capsule and the inner surface; and (c) diagnose an abnormal medical condition of the inner surface of the lumen by detecting a portion of the inner surface that is substantially less contractile in response to the electrical current, compared to normal tissue comprising the inner surface.

48. The method of claim 43, wherein the lumen comprises an esophagus of a patient, and wherein the step of introducing the capsule comprises the step of enabling the patient to swallow the capsule with a liquid.

49. The method of claim 43, further comprising the step of analyzing the image with a spectral analyzer that responds to a range of wavelengths from an ultraviolet waveband to an infrared waveband.

50. The method of claim 43, further comprising the step of determining a position of the capsule within the lumen by at least one of:
   (a) sensing a signal indicative of the position of the capsule within the lumen;
   (b) measuring a length of the tether that has been advanced into the lumen; and
   (c) determining the position based upon a content of the image that is produced that indicates one of an anatomical feature and a medical condition within the lumen.

51. The method of claim 43, further comprising the step of administering a therapy to the lumen using the capsule.

52. The method of claim 43, further comprising the steps of:
   (a) producing a plurality of overlapping images with the scanner; and
   (b) combining the plurality of overlapping images to produce a composite image of a substantially larger area than is encompassed by a single image.

53. The method of claim 43, further comprising the step of employing a plurality of scanners disposed in the capsule to achieve at least one of the following results:
   (a) scanning different regions of the lumen with each of the plurality of scanners;
   (b) producing a stereoscopic view of an inner surface of the lumen;
   (c) implementing a diagnostic function by detecting light in different wavebands received from the inner surface of the lumen;
   (d) rendering a therapeutic function;
   (e) monitoring the lumen for at least one of controlling a therapy being rendered, and assessing a condition of the lumen after the therapy has been administered; and
   (f) providing additional illumination for imaging the interior surface of the lumen.

54. The method of claim 43, further comprising the step of employing a sensor associated with the capsule for monitoring a parameter related to the lumen.

55. The method of claim 54, wherein the parameter comprises one of:
   (a) a chemical level;
   (b) a pressure exerted by walls of the lumen; and
   (c) a temperature.

56. The method of claim 43, further comprising the step of enabling a user to enable the capsule to pass through the lumen without further constraint from the tether by one of the steps of:
   (a) releasing a proximal end of the tether so that the tether and the capsule move through the lumen; and
   (b) releasing the capsule from the tether so that the capsule can move through the lumen.

57. The method of claim 43, further comprising the step of retrieving the capsule by one of the steps of:
   (a) enabling the capsule to pass through the lumen and be expelled from the body; and
   (b) withdrawing the capsule from the lumen by applying force to the tether.

58. The method of claim 43, further comprising the step of enabling a user to rotate the capsule by rotating the tether connected thereto.

59. An imaging probe for producing images of a surface within a body lumen, comprising:
   (a) a capsule disposed at a distal end of the imaging probe, said capsule being sized to enable the capsule to be readily introduced into a body lumen and including an imaging device for producing a signal that is usable to display an image of an inner surface within a body lumen;
   (b) a tether having a proximal end, and a distal end that is coupled to the capsule, said tether being flexible and substantially smaller in diameter than the capsule and being employed for moving the capsule and for conveying signals produced by the imaging device for use in displaying an image of an inner surface of a body lumen; and
   (c) means for reproducibly tracking a distance through which the capsule moves within the body lumen.

60. The imaging probe of claim 59, wherein the tether conveys at least one signal from the capsule toward the proximal end of the tether, wherein the at least one signal is selected from the group consisting of an electrical signal, and an optical signal from the capsule.

61. The imaging probe of claim 59, wherein the tether conveys at least one signal from the proximal end of the tether to the capsule, wherein the at least one signal is selected from the group consisting of an electrical signal, and an optical signal.

62. The imaging probe of claim 59, wherein the capsule is sized and configured to enable it to be readily swallowed down an esophagus of a patient, to enable imaging of a wall of an esophagus.

63. The imaging probe of claim 62, wherein the tether is sufficiently small in cross-sectional size and sufficiently flexible to enable it to readily follow the capsule down an esophagus of a patient when the capsule is swallowed.

64. The imaging probe of claim 59, wherein the signal produced by the imaging device in the capsule that enables display of an image of an inner surface of a body lumen is one of an electrical signal conveyed by a conductor disposed in the tether and an optical signal that is conveyed through an optical fiber in the tether, for use in externally displaying the image.

65. A capsular system for scanning an inner surface within a body lumen, comprising:
   (a) a capsule disposed at a distal end of the capsular system, said capsule being sized to enable the capsule to be readily introduced into a body lumen and including a scanning device for producing a signal that is usable to display an image of an inner surface within the body lumen, said scanning device being coupled to a light source and being configured to scan the inner surface within the body lumen in a desired scanning pattern with a beam of light; and
   (b) a tether having a proximal end, and a distal end that is coupled to the capsule, said tether being flexible and substantially smaller in diameter than the capsule and being employed for moving the capsule and for conveying signals produced by the scanning device, for use in displaying an image of the inner surface of the body lumen.

66. Apparatus for imaging an inner surface of a lumen within a body, comprising:
- (a) a capsule housing that is sized to readily pass through the lumen, at least a portion of the capsule housing being optically transparent;
- (b) a light source;
- (c) a scanner disposed within the capsule housing and coupled to the light source, the scanner having an actuator that drives the scanner to scan an inner surface of a lumen in a body with a beam of light that moves in a desired scanning pattern;
- (d) at least one light sensor that responds to light that has been reflected from an inner surface of a lumen, producing an electrical signal that is indicative of an intensity of the light;
- (e) an optical system that focuses the light used for scanning in the desired scanning pattern onto a portion of an inner surface of a lumen;
- (f) a tether that is connected to the capsule housing and which is configured to extend proximally through a lumen to enable a force to be applied to the capsule housing to control a movement of the capsule housing; and
- (g) an inflatable balloon coupled to the capsule, the balloon being inflated to at least one of:
  - (i) enable peristaltic advancement of the balloon with the capsule through a lumen in a body by forces applied by the lumen on the balloon when the balloon is at least partially inflated;
  - (ii) convey a fluid pressure from a wall of a lumen in which the balloon is disposed, to a pressure sensor that enables a pressure exerted thereby on the balloon to be monitored;
  - (iii) prevent further movement of the capsule housing through a lumen having a cross-sectional size that is smaller than that of the balloon when the balloon is at least partially inflated; and
  - (iv) generally center the capsule housing within a lumen of a body.

67. A method for scanning an inner surface of a lumen in a body, comprising the steps of:
- (a) introducing a capsule that includes a scanner into the lumen, the capsule being coupled to a tether;
- (b) enabling the capsule to advance through the lumen, with a proximal end of the tether remaining outside the lumen;
- (c) controlling a disposition of the capsule within the lumen by exerting a force on the tether;
- (d) producing an image of the inner surface of the lumen with the scanner; and
- (e) enabling a user to selectively allow the capsule to pass through the lumen without further constraint from the tether by carrying out one of the steps of:
  - (i) releasing the proximal end of the tether so that both the tether and the capsule can move through the lumen; and
  - (ii) releasing the capsule from the tether so that the capsule can move through the lumen free of the tether.

* * * * *